(12) United States Patent
Onishi et al.

(10) Patent No.: US 10,017,788 B2
(45) Date of Patent: Jul. 10, 2018

(54) RECOMBINANT YEAST AND METHOD FOR PRODUCING ETHANOL USING THE SAME

(71) Applicant: TOYOTA JIDOSHA KABUSHIKI KAISHA, Toyota-shi, Aichi (JP)

(72) Inventors: Toru Onishi, Toyota (JP); Nobuki Tada, Nisshin (JP); Satoshi Katahira, Nagoya (JP); Risa Nagura, Toyota (JP); Nobuhiro Ishida, Seto (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 0 days.

(21) Appl. No.: 14/772,637

(22) PCT Filed: Jun. 9, 2014

(86) PCT No.: PCT/JP2014/003069
§ 371 (c)(1),
(2) Date: Sep. 3, 2015

(87) PCT Pub. No.: WO2014/199623
PCT Pub. Date: Dec. 18, 2014

(65) Prior Publication Data
US 2016/0122784 A1 May 5, 2016

(30) Foreign Application Priority Data

Jun. 13, 2013 (JP) ................................. 2013-124755

(51) Int. Cl.
*C12N 9/04* (2006.01)
*C12P 7/06* (2006.01)
*C12N 9/92* (2006.01)
*C12P 7/10* (2006.01)

(52) U.S. Cl.
CPC .............. *C12P 7/06* (2013.01); *C12N 9/0006* (2013.01); *C12N 9/92* (2013.01); *C12P 7/10* (2013.01); *C12P 2203/00* (2013.01); *C12Y 101/01086* (2013.01); *C12Y 503/01005* (2013.01); *Y02E 50/16* (2013.01); *Y02E 50/17* (2013.01)

(58) Field of Classification Search
CPC .................................................. C12N 9/0006

USPC ........................................................ 435/252.3
See application file for complete search history.

(56) References Cited

U.S. PATENT DOCUMENTS

2013/0095538 A1    4/2013  Katahira et al.

FOREIGN PATENT DOCUMENTS

| CN | 102791858 A | 11/2012 |
| JP | 2005-514951 A | 5/2005 |
| JP | 2010-239925 A | 10/2010 |
| WO | 03/062430 A1 | 7/2003 |
| WO | 03/078643 A1 | 9/2003 |
| WO | 2011/078262 A1 | 6/2011 |

OTHER PUBLICATIONS

Dawid Brat, et al., "Isobutanol production from D-xylose by recombinant *Saccharomyces cerevisiae*", FEMS Yeast Res., 2013, pp. 241-244, vol. 13.
International Search Report of PCT/JP2014/003069, dated Oct. 21, 2014. [PCT/ISA/210].
Marco Sonderegger, et al., "Metabolic Engineering of a Phosphoketolase Pathway for Pentose Catabolism in *Saccharomyces cerevisiae*," Applied and Environmental Microbiology, May 2004, pp. 2892-2897, vol. 70, No. 5.
Written Opinion of PCT/JP2014/003069, dated Oct. 21, 2014. [PCT/ISA/237].
Lee, et al., "Directed Evolution of Xylose Isomerase for Improved Xylose Catabolism and Fermentation in the Yeast *Saccharomyces cerevisiae*," Applied and Environmental Microbiology 78(16):5708-5716 (Aug. 2012).
Rane, et al., "Reversal of the Nucleotide Specificity of Ketol Acid Reductoisomerase by Site-Directed Mutagenesis Identifies the NADPH Binding Site," Archives of Biochemistry and Biophysics 338(1):83-89 (Feb. 1, 1997).

*Primary Examiner* — Maryam Monshipouri
(74) *Attorney, Agent, or Firm* — Sughrue Mion, PLLC

(57) ABSTRACT

The invention is intended to improve xylose assimilation ability and ethanol fermentation ability in a xylose-assimilating yeast into which a xylose isomerase gene has been introduced. The amount of NADH produced by the recombinant yeast into which the xylose isomerase gene had been introduced as a result of the enzymatic reaction of acetohydroxy acid reductoisomerase is lowered.

5 Claims, 5 Drawing Sheets

SEQUENCE LISTING

<160> NUMBER OF SEQ ID NOS: 52

<210> SEQ ID NO 1
<211> LENGTH: 1188
<212> TYPE: DNA
<213> ORGANISM: Saccharomyces cerevisiae
<220> FEATURE:
<221> NAME/KEY: CDS
<222> LOCATION: (1)..(1188)

<400> SEQUENCE: 1

-continued

| | |
|---|---|
| atg ttg aga act caa gcc gcc aga ttg atc tgc aac tcc cgt gtc atc<br>Met Leu Arg Thr Gln Ala Ala Arg Leu Ile Cys Asn Ser Arg Val Ile<br>1               5                   10                  15 | 48 |
| act gct aag aga acc ttt gct ttg gcc acc cgt gct gct gct tac agc<br>Thr Ala Lys Arg Thr Phe Ala Leu Ala Thr Arg Ala Ala Ala Tyr Ser<br>            20                  25                  30 | 96 |
| aga cca gct gcc cgt ttc gtt aag cca atg atc act acc cgt ggt ttg<br>Arg Pro Ala Ala Arg Phe Val Lys Pro Met Ile Thr Thr Arg Gly Leu<br>        35                  40                  45 | 144 |
| aag caa atc aac ttc ggt ggt act gtt gaa acc gtc tac gaa aga gct<br>Lys Gln Ile Asn Phe Gly Gly Thr Val Glu Thr Val Tyr Glu Arg Ala<br>    50                  55                  60 | 192 |
| gac tgg cca aga gaa aag ttg ttg gac tac ttc aag aac gac act ttt<br>Asp Trp Pro Arg Glu Lys Leu Leu Asp Tyr Phe Lys Asn Asp Thr Phe<br>65                  70                  75                  80 | 240 |
| gct ttg atc ggt tac ggt tcc caa ggt tac ggt caa ggt ttg aac ttg<br>Ala Leu Ile Gly Tyr Gly Ser Gln Gly Tyr Gly Gln Gly Leu Asn Leu<br>                85                  90                  95 | 288 |
| aga gac aac ggt ttg aac gtt atc att ggt gtc cgt aaa gat ggt gct<br>Arg Asp Asn Gly Leu Asn Val Ile Ile Gly Val Arg Lys Asp Gly Ala<br>            100                 105                 110 | 336 |
| tct tgg aag gct gcc atc gaa gac ggt tgg gtt cca ggc aag aac ttg<br>Ser Trp Lys Ala Ala Ile Glu Asp Gly Trp Val Pro Gly Lys Asn Leu<br>        115                 120                 125 | 384 |
| ttc act gtt gaa gat gct atc aag aga ggt agt tac gtt atg aac ttg<br>Phe Thr Val Glu Asp Ala Ile Lys Arg Gly Ser Tyr Val Met Asn Leu<br>    130                 135                 140 | 432 |
| ttg tcc gat gcc gct caa tca gaa acc tgg cct gct atc aag cca ttg<br>Leu Ser Asp Ala Ala Gln Ser Glu Thr Trp Pro Ala Ile Lys Pro Leu<br>145                 150                 155                 160 | 480 |
| ttg acc aag ggt aag act ttg tac ttc tcc cac ggt ttc tcc cca gtc<br>Leu Thr Lys Gly Lys Thr Leu Tyr Phe Ser His Gly Phe Ser Pro Val<br>                165                 170                 175 | 528 |
| ttc aag gac ttg act cac gtt gaa cca cca aag gac tta gat gtt atc<br>Phe Lys Asp Leu Thr His Val Glu Pro Pro Lys Asp Leu Asp Val Ile<br>            180                 185                 190 | 576 |
| ttg gtt gct cca aag ggt tcc ggt aga act gtc aga tct ttg ttc aag<br>Leu Val Ala Pro Lys Gly Ser Gly Arg Thr Val Arg Ser Leu Phe Lys<br>        195                 200                 205 | 624 |
| gaa ggt cgt ggt att aac tct tct tac gcc gtc tgg aac gat gtc acc<br>Glu Gly Arg Gly Ile Asn Ser Ser Tyr Ala Val Trp Asn Asp Val Thr<br>    210                 215                 220 | 672 |
| ggt aag gct cac gaa aag gcc caa gct ttg gcc gtt gcc att ggt tcc<br>Gly Lys Ala His Glu Lys Ala Gln Ala Leu Ala Val Ala Ile Gly Ser<br>225                 230                 235                 240 | 720 |
| ggt tac gtt tac caa acc act ttc gaa aga gaa gtc aac tct gac ttg<br>Gly Tyr Val Tyr Gln Thr Thr Phe Glu Arg Glu Val Asn Ser Asp Leu<br>                245                 250                 255 | 768 |
| tac ggt gaa aga ggt tgt tta atg ggt ggt atc cac ggt atg ttc ttg<br>Tyr Gly Glu Arg Gly Cys Leu Met Gly Gly Ile His Gly Met Phe Leu<br>            260                 265                 270 | 816 |
| gct caa tac gac gtc ttg aga gaa aac ggt cac tcc cca tct gaa gct<br>Ala Gln Tyr Asp Val Leu Arg Glu Asn Gly His Ser Pro Ser Glu Ala<br>        275                 280                 285 | 864 |
| ttc aac gaa acc gtc gaa gaa gct acc caa tct cta tac cca ttg atc<br>Phe Asn Glu Thr Val Glu Glu Ala Thr Gln Ser Leu Tyr Pro Leu Ile<br>    290                 295                 300 | 912 |
| ggt aag tac ggt atg gat tac atg tac gat gct tgt tcc acc acc gcc<br>Gly Lys Tyr Gly Met Asp Tyr Met Tyr Asp Ala Cys Ser Thr Thr Ala | 960 |

|     |     |     |     |     |     |     |     |     |     |     |     |      |
|-----|-----|-----|-----|-----|-----|-----|-----|-----|-----|-----|-----|------|
| 305 |     |     |     |     | 310 |     |     |     | 315 |     |     | 320  |
| aga | aga | ggt | gct | ttg | gac | tgg | tac | cca | atc | ttc | aag | aat gct ttg aag | 1008 |
| Arg | Arg | Gly | Ala | Leu | Asp | Trp | Tyr | Pro | Ile | Phe | Lys | Asn Ala Leu Lys |
|     |     |     |     | 325 |     |     |     | 330 |     |     |     | 335  |
| cct | gtt | ttc | caa | gac | ttg | tac | gaa | tct | acc | aag | aac | ggt acc gaa acc | 1056 |
| Pro | Val | Phe | Gln | Asp | Leu | Tyr | Glu | Ser | Thr | Lys | Asn | Gly Thr Glu Thr |
|     |     |     | 340 |     |     |     | 345 |     |     |     | 350 |      |
| aag | aga | tct | ttg | gaa | ttc | aac | tct | caa | cct | gac | tac | aga gaa aag cta | 1104 |
| Lys | Arg | Ser | Leu | Glu | Phe | Asn | Ser | Gln | Pro | Asp | Tyr | Arg Glu Lys Leu |
|     |     | 355 |     |     |     | 360 |     |     |     | 365 |     |      |
| gaa | aag | gaa | tta | gac | acc | atc | aga | aac | atg | gaa | atc | tgg aag gtt ggt | 1152 |
| Glu | Lys | Glu | Leu | Asp | Thr | Ile | Arg | Asn | Met | Glu | Ile | Trp Lys Val Gly |
|     | 370 |     |     |     | 375 |     |     |     | 380 |     |     |      |
| aag | gaa | gtc | aga | aag | ttg | aga | cca | gaa | aac | caa | taa |      | 1188 |
| Lys | Glu | Val | Arg | Lys | Leu | Arg | Pro | Glu | Asn | Gln |     |      |
| 385 |     |     |     |     | 390 |     |     |     | 395 |     |     |      |

<210> SEQ ID NO 2
<211> LENGTH: 395
<212> TYPE: PRT
<213> ORGANISM: Saccharomyces cerevisiae

<400> SEQUENCE: 2

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu

```
                260                 265                 270
Ala Gln Tyr Asp Val Leu Arg Glu Asn Gly His Ser Pro Ser Glu Ala
            275                 280                 285

Phe Asn Glu Thr Val Glu Glu Ala Thr Gln Ser Leu Tyr Pro Leu Ile
            290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
            355                 360                 365

Glu Lys Glu Leu Asp Thr Ile Arg Asn Met Glu Ile Trp Lys Val Gly
            370                 375                 380

Lys Glu Val Arg Lys Leu Arg Pro Glu Asn Gln
385                 390                 395

<210> SEQ ID NO 3
<211> LENGTH: 1476
<212> TYPE: DNA
<213> ORGANISM: Escherichia coli
<220> FEATURE:
<221> NAME/KEY: CDS
<222> LOCATION: (1)..(1476)

<400> SEQUENCE: 3
```

| | | | | | | | | | | | | | | | | |
|---|---|---|---|---|---|---|---|---|---|---|---|---|---|---|---|---|
| atg | gca | aac | tac | ttc | aac | act | ttg | aat | ttg | aga | caa | caa | ttg | gct | caa | 48 |
| Met | Ala | Asn | Tyr | Phe | Asn | Thr | Leu | Asn | Leu | Arg | Gln | Gln | Leu | Ala | Gln | |
| 1 | | | | 5 | | | | | 10 | | | | | 15 | | |
| ttg | ggt | aaa | tgt | aga | ttc | atg | ggt | aga | gat | gaa | ttc | gct | gat | ggt | gca | 96 |
| Leu | Gly | Lys | Cys | Arg | Phe | Met | Gly | Arg | Asp | Glu | Phe | Ala | Asp | Gly | Ala | |
| | | | 20 | | | | | 25 | | | | | 30 | | | |
| tct | tac | ttg | caa | ggt | aaa | aag | gtt | gtt | att | gtt | ggt | tgt | ggt | gca | caa | 144 |
| Ser | Tyr | Leu | Gln | Gly | Lys | Lys | Val | Val | Ile | Val | Gly | Cys | Gly | Ala | Gln | |
| | | 35 | | | | | 40 | | | | | 45 | | | | |
| ggt | ttg | aac | caa | ggt | ttg | aac | atg | aga | gat | tct | ggt | ttg | gat | atc | tca | 192 |
| Gly | Leu | Asn | Gln | Gly | Leu | Asn | Met | Arg | Asp | Ser | Gly | Leu | Asp | Ile | Ser | |
| | 50 | | | | | 55 | | | | | 60 | | | | | |
| tac | gct | ttg | gat | ttg | gaa | gca | att | gct | gaa | gtt | gat | gct | tca | tgg | aga | 240 |
| Tyr | Ala | Leu | Asp | Leu | Glu | Ala | Ile | Ala | Glu | Val | Asp | Ala | Ser | Trp | Arg | |
| 65 | | | | | 70 | | | | | 75 | | | | | 80 | |
| aaa | gca | aca | gaa | aat | ggt | ttc | aag | gtt | ggt | act | tac | gaa | gaa | ttg | att | 288 |
| Lys | Ala | Thr | Glu | Asn | Gly | Phe | Lys | Val | Gly | Thr | Tyr | Glu | Glu | Leu | Ile | |
| | | | | 85 | | | | | 90 | | | | | 95 | | |
| cca | caa | gct | gat | ttg | gtt | att | aac | tta | act | cct | gat | aag | caa | cat | tcc | 336 |
| Pro | Gln | Ala | Asp | Leu | Val | Ile | Asn | Leu | Thr | Pro | Asp | Lys | Gln | His | Ser | |
| | | | 100 | | | | | 105 | | | | | 110 | | | |
| gat | gtt | gtt | aga | aca | gtt | caa | cca | ttg | atg | aaa | gat | ggt | gct | gca | ttg | 384 |
| Asp | Val | Val | Arg | Thr | Val | Gln | Pro | Leu | Met | Lys | Asp | Gly | Ala | Ala | Leu | |
| | | 115 | | | | | 120 | | | | | 125 | | | | |
| ggt | tac | agt | cat | ggt | ttt | aat | atc | gtt | gaa | gtt | ggt | gaa | caa | atc | aga | 432 |
| Gly | Tyr | Ser | His | Gly | Phe | Asn | Ile | Val | Glu | Val | Gly | Glu | Gln | Ile | Arg | |
| | 130 | | | | | 135 | | | | | 140 | | | | | |
| aag | gat | atc | acc | gtt | gtt | atg | gtt | gct | cca | aaa | tgt | cct | ggt | act | gaa | 480 |
| Lys | Asp | Ile | Thr | Val | Val | Met | Val | Ala | Pro | Lys | Cys | Pro | Gly | Thr | Glu | |
| 145 | | | | | 150 | | | | | 155 | | | | | 160 | |
| gtt | aga | gaa | gaa | tac | aag | aga | ggt | ttc | ggt | gtt | cct | aca | ttg | att | gct | 528 |
| Val | Arg | Glu | Glu | Tyr | Lys | Arg | Gly | Phe | Gly | Val | Pro | Thr | Leu | Ile | Ala | |

```
                    165                 170                 175
gtt cat cca gaa aat gat cct aaa ggt gag ggt atg gca att gct aag      576
Val His Pro Glu Asn Asp Pro Lys Gly Glu Gly Met Ala Ile Ala Lys
        180                 185                 190 gca tgg gct gca gct acc ggt ggt cat aga gct ggt gtt ttg gaa tct      624
Ala Trp Ala Ala Ala Thr Gly Gly His Arg Ala Gly Val Leu Glu Ser
            195                 200                 205 tca ttc gtt gca gag gtt aag tct gat ttg atg ggt gaa caa acc att      672
Ser Phe Val Ala Glu Val Lys Ser Asp Leu Met Gly Glu Gln Thr Ile
210                 215                 220 ttg tgt ggc atg tta caa gct ggt tca ttg ttg tgt ttc gat aag ttg      720
Leu Cys Gly Met Leu Gln Ala Gly Ser Leu Leu Cys Phe Asp Lys Leu
225                 230                 235                 240 gtt gaa gaa ggt act gat cca gct tat gca gaa aaa ttg att caa ttc      768
Val Glu Glu Gly Thr Asp Pro Ala Tyr Ala Glu Lys Leu Ile Gln Phe
                245                 250                 255 ggt tgg gaa act att aca gaa gct tta aag caa ggt ggt atc act ttg      816
Gly Trp Glu Thr Ile Thr Glu Ala Leu Lys Gln Gly Gly Ile Thr Leu
            260                 265                 270 atg atg gat aga ttg tct aat cca gca aaa ttg aga gct tac gca ttg      864
Met Met Asp Arg Leu Ser Asn Pro Ala Lys Leu Arg Ala Tyr Ala Leu
        275                 280                 285 tca gaa caa ttg aag gaa atc atg gct cct ttg ttc caa aag cat atg      912
Ser Glu Gln Leu Lys Glu Ile Met Ala Pro Leu Phe Gln Lys His Met
290                 295                 300 gat gat atc att tcc ggt gaa ttc tcc agt ggt atg atg gct gat tgg      960
Asp Asp Ile Ile Ser Gly Glu Phe Ser Ser Gly Met Met Ala Asp Trp
305                 310                 315                 320 gca aac gat gat aaa aag ttg ttg aca tgg aga gaa gaa acc ggt aaa     1008
Ala Asn Asp Asp Lys Lys Leu Leu Thr Trp Arg Glu Glu Thr Gly Lys
                325                 330                 335 act gct ttt gaa acc gca cca caa tac gaa ggt aaa atc ggt gaa caa     1056
Thr Ala Phe Glu Thr Ala Pro Gln Tyr Glu Gly Lys Ile Gly Glu Gln
            340                 345                 350 gaa tac ttc gat aag ggt gtt ttg atg att gct atg gtt aaa gca ggt     1104
Glu Tyr Phe Asp Lys Gly Val Leu Met Ile Ala Met Val Lys Ala Gly
        355                 360                 365 gtt gaa ttg gca ttc gaa aca atg gtt gat tca ggt atc att gaa gaa     1152
Val Glu Leu Ala Phe Glu Thr Met Val Asp Ser Gly Ile Ile Glu Glu
370                 375                 380 tcc gct tat tac gaa agt ttg cat gaa ttg cct tta att gct aac act     1200
Ser Ala Tyr Tyr Glu Ser Leu His Glu Leu Pro Leu Ile Ala Asn Thr
385                 390                 395                 400 att gca aga aag aga ttg tac gaa atg aac gtt gtt att tcc gat aca     1248
Ile Ala Arg Lys Arg Leu Tyr Glu Met Asn Val Val Ile Ser Asp Thr
                405                 410                 415 gct gaa tac ggt aac tat ttg ttt tct tac gca tgt gtt cca ttg tta     1296
Ala Glu Tyr Gly Asn Tyr Leu Phe Ser Tyr Ala Cys Val Pro Leu Leu
            420                 425                 430 aag cct ttc atg gct gaa ttg caa cct ggt gac ttg ggt aaa gct att     1344
Lys Pro Phe Met Ala Glu Leu Gln Pro Gly Asp Leu Gly Lys Ala Ile
        435                 440                 445 cct gaa ggt gca gtt gat aac ggt caa ttg aga gat gtt aac gaa gct     1392
Pro Glu Gly Ala Val Asp Asn Gly Gln Leu Arg Asp Val Asn Glu Ala
450                 455                 460 atc aga tct cat gca atc gaa caa gtt ggt aaa aag ttg aga ggt tac     1440
Ile Arg Ser His Ala Ile Glu Gln Val Gly Lys Lys Leu Arg Gly Tyr
465                 470                 475                 480 atg aca gat atg aag aga atc gct gtt gca ggt taa                     1476
Met Thr Asp Met Lys Arg Ile Ala Val Ala Gly
```

```
Met Thr Asp Met Lys Arg Ile Ala Val Ala Gly
            485                 490
```

<210> SEQ ID NO 4
<211> LENGTH: 491
<212> TYPE: PRT
<213> ORGANISM: Escherichia coli

<400> SEQUENCE: 4

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Asp Leu Glu Ala Ile Ala Glu Val Asp Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365
```

```
Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
                420                 425                 430

Lys Pro Phe Met Ala Glu Leu Gln Pro Gly Asp Leu Gly Lys Ala Ile
            435                 440                 445

Pro Glu Gly Ala Val Asp Asn Gly Gln Leu Arg Asp Val Asn Glu Ala
            450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 5
<211> LENGTH: 1476
<212> TYPE: DNA
<213> ORGANISM: Escherichia coli
<220> FEATURE:
<221> NAME/KEY: CDS
<222> LOCATION: (1)..(1476)

<400> SEQUENCE: 5
```

| | | | | | | | | | | | | | | | | |
|---|---|---|---|---|---|---|---|---|---|---|---|---|---|---|---|---|
| atg | gca | aac | tac | ttc | aac | act | ttg | aat | ttg | aga | caa | caa | ttg | gct | caa | 48 |
| Met | Ala | Asn | Tyr | Phe | Asn | Thr | Leu | Asn | Leu | Arg | Gln | Gln | Leu | Ala | Gln | |
| 1 | | | | 5 | | | | | 10 | | | | | 15 | | |
| ttg | ggt | aaa | tgt | aga | ttc | atg | ggt | aga | gat | gaa | ttc | gct | gat | ggt | gca | 96 |
| Leu | Gly | Lys | Cys | Arg | Phe | Met | Gly | Arg | Asp | Glu | Phe | Ala | Asp | Gly | Ala | |
| | | 20 | | | | | 25 | | | | | 30 | | | | |
| tct | tac | ttg | caa | ggt | aaa | aag | gtt | gtt | att | gtt | ggt | tgt | ggt | gca | caa | 144 |
| Ser | Tyr | Leu | Gln | Gly | Lys | Lys | Val | Val | Ile | Val | Gly | Cys | Gly | Ala | Gln | |
| | | | 35 | | | | | 40 | | | | | 45 | | | |
| ggt | ttg | aac | caa | ggt | ttg | aac | atg | aga | gat | tct | ggt | ttg | gat | atc | tca | 192 |
| Gly | Leu | Asn | Gln | Gly | Leu | Asn | Met | Arg | Asp | Ser | Gly | Leu | Asp | Ile | Ser | |
| | 50 | | | | | 55 | | | | | 60 | | | | | |
| tac | gct | ttg | aga | aag | gaa | tct | att | gct | gaa | aag | gat | gct | gat | tgg | aga | 240 |
| Tyr | Ala | Leu | Arg | Lys | Glu | Ser | Ile | Ala | Glu | Lys | Asp | Ala | Asp | Trp | Arg | |
| 65 | | | | | 70 | | | | | 75 | | | | | 80 | |
| aaa | gca | aca | gaa | aat | ggt | ttc | aag | gtt | ggt | act | tac | gaa | gaa | ttg | att | 288 |
| Lys | Ala | Thr | Glu | Asn | Gly | Phe | Lys | Val | Gly | Thr | Tyr | Glu | Glu | Leu | Ile | |
| | | | | 85 | | | | | 90 | | | | | 95 | | |
| cca | caa | gct | gat | ttg | gtt | att | aac | tta | act | cct | gat | aag | gtt | cat | tcc | 336 |
| Pro | Gln | Ala | Asp | Leu | Val | Ile | Asn | Leu | Thr | Pro | Asp | Lys | Val | His | Ser | |
| | | | 100 | | | | | 105 | | | | | 110 | | | |
| gat | gtt | gtt | aga | aca | gtt | caa | cca | ttg | atg | aaa | gat | ggt | gct | gca | ttg | 384 |
| Asp | Val | Val | Arg | Thr | Val | Gln | Pro | Leu | Met | Lys | Asp | Gly | Ala | Ala | Leu | |
| | | 115 | | | | | 120 | | | | | 125 | | | | |
| ggt | tac | agt | cat | ggt | ttt | aat | atc | gtt | gaa | gtt | ggt | gaa | caa | atc | aga | 432 |
| Gly | Tyr | Ser | His | Gly | Phe | Asn | Ile | Val | Glu | Val | Gly | Glu | Gln | Ile | Arg | |
| | 130 | | | | | 135 | | | | | 140 | | | | | |
| aag | ggt | atc | acc | gtt | gtt | atg | gtt | gct | cca | aaa | tgt | cct | ggt | act | gaa | 480 |
| Lys | Gly | Ile | Thr | Val | Val | Met | Val | Ala | Pro | Lys | Cys | Pro | Gly | Thr | Glu | |
| 145 | | | | | 150 | | | | | 155 | | | | | 160 | |
| gtt | aga | gaa | gaa | tac | aag | aga | ggt | ttc | ggt | gtt | cct | aca | ttg | att | gct | 528 |
| Val | Arg | Glu | Glu | Tyr | Lys | Arg | Gly | Phe | Gly | Val | Pro | Thr | Leu | Ile | Ala | |
| | | | | 165 | | | | | 170 | | | | | 175 | | |

```
gtt cat cca gaa aat gat cct aaa aga gag ggt atg gca att gct aag      576
Val His Pro Glu Asn Asp Pro Lys Arg Glu Gly Met Ala Ile Ala Lys
        180                 185                 190 gca tgg gct gca gct acc ggt ggt cat aga gct ggt gtt ttg gaa tct      624
Ala Trp Ala Ala Ala Thr Gly Gly His Arg Ala Gly Val Leu Glu Ser
    195                 200                 205 tca ttc gtt gca gag gtt aag tct gat ttg atg ggt gaa caa acc att      672
Ser Phe Val Ala Glu Val Lys Ser Asp Leu Met Gly Glu Gln Thr Ile
210                 215                 220 ttg tgt ggc atg tta caa gct ggt tca ttg ttg tgt ttc gat aag ttg      720
Leu Cys Gly Met Leu Gln Ala Gly Ser Leu Leu Cys Phe Asp Lys Leu
225                 230                 235                 240 gtt gaa gaa ggt act gat cca gct tat gca gaa aaa ttg att caa ttc      768
Val Glu Glu Gly Thr Asp Pro Ala Tyr Ala Glu Lys Leu Ile Gln Phe
                245                 250                 255 ggt tgg gaa act att aca gaa gct tta aag caa ggt ggt atc act ttg      816
Gly Trp Glu Thr Ile Thr Glu Ala Leu Lys Gln Gly Gly Ile Thr Leu
            260                 265                 270 atg atg gat aga ttg tct aat cca gca aaa ttg aga gct tac gca ttg      864
Met Met Asp Arg Leu Ser Asn Pro Ala Lys Leu Arg Ala Tyr Ala Leu
        275                 280                 285 tca gaa caa ttg aag gaa atc atg gct cct ttg ttc caa aag cat atg      912
Ser Glu Gln Leu Lys Glu Ile Met Ala Pro Leu Phe Gln Lys His Met
    290                 295                 300 gat gat atc att tcc ggt gaa ttc tcc agt ggt atg atg gct gat tgg      960
Asp Asp Ile Ile Ser Gly Glu Phe Ser Ser Gly Met Met Ala Asp Trp
305                 310                 315                 320 gca aac gat gat aaa aag ttg ttg aca tgg aga gaa gaa acc ggt aaa     1008
Ala Asn Asp Asp Lys Lys Leu Leu Thr Trp Arg Glu Glu Thr Gly Lys
                325                 330                 335 act gct ttt gaa acc gca cca caa tac gaa ggt aaa atc ggt gaa caa     1056
Thr Ala Phe Glu Thr Ala Pro Gln Tyr Glu Gly Lys Ile Gly Glu Gln
            340                 345                 350 gaa tac ttc gat aag ggt gtt ttg atg att gct atg gtt aaa gca ggt     1104
Glu Tyr Phe Asp Lys Gly Val Leu Met Ile Ala Met Val Lys Ala Gly
        355                 360                 365 gtt gaa ttg gca ttc gaa aca atg gtt gat tca ggt atc att gaa gaa     1152
Val Glu Leu Ala Phe Glu Thr Met Val Asp Ser Gly Ile Ile Glu Glu
    370                 375                 380 tcc gct tat tac gaa agt ttg cat gaa ttg cct tta att gct aac act     1200
Ser Ala Tyr Tyr Glu Ser Leu His Glu Leu Pro Leu Ile Ala Asn Thr
385                 390                 395                 400 att gca aga aag aga ttg tac gaa atg aac gtt gtt att tcc gat aca     1248
Ile Ala Arg Lys Arg Leu Tyr Glu Met Asn Val Val Ile Ser Asp Thr
                405                 410                 415 gct gaa tac ggt aac tat ttg ttt tct tac gca tgt gtt cca ttg tta     1296
Ala Glu Tyr Gly Asn Tyr Leu Phe Ser Tyr Ala Cys Val Pro Leu Leu
            420                 425                 430 aag cct ttc atg gct gaa ttg caa cct ggt gac ttg ggt aaa gct att     1344
Lys Pro Phe Met Ala Glu Leu Gln Pro Gly Asp Leu Gly Lys Ala Ile
        435                 440                 445 cct gaa ggt gca gtt gat aac ggt caa ttg aga gat gtt aac gaa gct     1392
Pro Glu Gly Ala Val Asp Asn Gly Gln Leu Arg Asp Val Asn Glu Ala
    450                 455                 460 atc aga tct cat gca atc gaa caa gtt ggt aaa aag ttg aga ggt tac     1440
Ile Arg Ser His Ala Ile Glu Gln Val Gly Lys Lys Leu Arg Gly Tyr
465                 470                 475                 480 atg aca gat atg aag aga atc gct gtt gca ggt taa                     1476
Met Thr Asp Met Lys Arg Ile Ala Val Ala Gly
```

<210> SEQ ID NO 6
<211> LENGTH: 491
<212> TYPE: PRT
<213> ORGANISM: Escherichia coli

<400> SEQUENCE: 6

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ser Ile Ala Glu Lys Asp Ala Asp Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Val His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Gly Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Arg Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365
```

```
Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
                435                 440                 445

Pro Glu Gly Ala Val Asp Asn Gly Gln Leu Arg Asp Val Asn Glu Ala
450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490
```

<210> SEQ ID NO 7
<211> LENGTH: 1320
<212> TYPE: DNA
<213> ORGANISM: Unknown
<220> FEATURE:
<223> OTHER INFORMATION: Obtained from Intestinal Protist of
      Reticulitermes speratus
<220> FEATURE:
<221> NAME/KEY: CDS
<222> LOCATION: (1)..(1320)

<400> SEQUENCE: 7

```
atg tct caa att ttt aag gat atc cca gtt att aaa tat gaa ggt cca      48
Met Ser Gln Ile Phe Lys Asp Ile Pro Val Ile Lys Tyr Glu Gly Pro
1               5                   10                  15 gct tcc aag aat cct ttg agt ttc aaa tac tac gat gca aac aag gtt      96
Ala Ser Lys Asn Pro Leu Ser Phe Lys Tyr Tyr Asp Ala Asn Lys Val
                20                  25                  30 att gat ggt aaa cca atg aag gaa cat ttg aga tac gca atg gct tgg     144
Ile Asp Gly Lys Pro Met Lys Glu His Leu Arg Tyr Ala Met Ala Trp
            35                  40                  45 tgg cat aat ttg tgt gct acc ggt caa gat atg ttt ggt cct ggt act     192
Trp His Asn Leu Cys Ala Thr Gly Gln Asp Met Phe Gly Pro Gly Thr
        50                  55                  60 gca gat aaa tcc ttc ggt agt aag aca gtt ggt acc atg gaa cat gca     240
Ala Asp Lys Ser Phe Gly Ser Lys Thr Val Gly Thr Met Glu His Ala
65                  70                  75                  80 cat gct aaa gtt gat gct ggt ttt gaa ttc atg tcc aag ttg ggt gtt     288
His Ala Lys Val Asp Ala Gly Phe Glu Phe Met Ser Lys Leu Gly Val
                85                  90                  95 gaa tac ttc tgt ttc cat gat gct gat ttg gtt cca gaa gca gat act     336
Glu Tyr Phe Cys Phe His Asp Ala Asp Leu Val Pro Glu Ala Asp Thr
                100                 105                 110 ttg agt gaa aca aac aaa aga ttg gat gaa atc gct gaa cat atc gtt     384
Leu Ser Glu Thr Asn Lys Arg Leu Asp Glu Ile Ala Glu His Ile Val
            115                 120                 125 gct aag caa aag gca act ggt att aaa tgt ttg tgg ggt aca gca aat     432
Ala Lys Gln Lys Ala Thr Gly Ile Lys Cys Leu Trp Gly Thr Ala Asn
        130                 135                 140 ttg ttt tct aac cct aga ttc tta aat ggt tct ggt tct tca aac tca     480
Leu Phe Ser Asn Pro Arg Phe Leu Asn Gly Ser Gly Ser Ser Asn Ser
145                 150                 155                 160 gct gat gtt tat gca tac gct gca gct caa att aaa aag gct ttg gat     528
```

```
                Ala Asp Val Tyr Ala Tyr Ala Ala Gln Ile Lys Lys Ala Leu Asp
                            165                 170                 175 ttg act gtt aaa ttt ggt ggt gtt ggt tat gtt ttc tgg ggt ggt aga         576
Leu Thr Val Lys Phe Gly Gly Val Gly Tyr Val Phe Trp Gly Gly Arg
            180                 185                 190 gaa ggt tac gaa acc ttg ttg aac act gat gtt aag ttc gaa caa gaa         624
Glu Gly Tyr Glu Thr Leu Leu Asn Thr Asp Val Lys Phe Glu Gln Glu
        195                 200                 205 aac atc gct aac ttg atg cat ttg gca gtt act tac ggt aga tca atc         672
Asn Ile Ala Asn Leu Met His Leu Ala Val Thr Tyr Gly Arg Ser Ile
    210                 215                 220 ggt ttt aaa ggt gac ttc tac att gaa cca aaa cct aag gaa cca aca         720
Gly Phe Lys Gly Asp Phe Tyr Ile Glu Pro Lys Pro Lys Glu Pro Thr
225                 230                 235                 240 aag cat caa tat gat ttt gat gca gct act aca att ggt ttc att aga         768
Lys His Gln Tyr Asp Phe Asp Ala Ala Thr Thr Ile Gly Phe Ile Arg
                245                 250                 255 caa tac ggt ttg gaa aag gat ttc aag ttg aac atc gaa gca aac cat         816
Gln Tyr Gly Leu Glu Lys Asp Phe Lys Leu Asn Ile Glu Ala Asn His
            260                 265                 270 gct aca tta gca ggt cat acc ttc caa cat gat ttg aga atc tct gct         864
Ala Thr Leu Ala Gly His Thr Phe Gln His Asp Leu Arg Ile Ser Ala
        275                 280                 285 att aat ggc atg tta ggt tca gtt gat gca aac aca ggt gac cca ttg         912
Ile Asn Gly Met Leu Gly Ser Val Asp Ala Asn Thr Gly Asp Pro Leu
    290                 295                 300 tta ggt tgg gat acc gat gaa ttt cct tat tcc gtt tac gat acc act         960
Leu Gly Trp Asp Thr Asp Glu Phe Pro Tyr Ser Val Tyr Asp Thr Thr
305                 310                 315                 320 ttg gct atg tac gaa att att aag gca ggt ggt ttg acc ggt ggt ttg        1008
Leu Ala Met Tyr Glu Ile Ile Lys Ala Gly Gly Leu Thr Gly Gly Leu
                325                 330                 335 aat ttt gat tcc aag gtt aga aga cca agt tac aca cat gaa gat ttg        1056
Asn Phe Asp Ser Lys Val Arg Arg Pro Ser Tyr Thr His Glu Asp Leu
            340                 345                 350 ttt tac ggt ttc att ttg ggt atg gat tct ttc gct ttg ggt ttg att        1104
Phe Tyr Gly Phe Ile Leu Gly Met Asp Ser Phe Ala Leu Gly Leu Ile
        355                 360                 365 aaa gca aag gct ttg att gca gat gga aga ttg gat tca ttc gtt aag        1152
Lys Ala Lys Ala Leu Ile Ala Asp Gly Arg Leu Asp Ser Phe Val Lys
    370                 375                 380 gat aga tac gct tct tac ggt tca ggt att ggt gct aag att aga gat        1200
Asp Arg Tyr Ala Ser Tyr Gly Ser Gly Ile Gly Ala Lys Ile Arg Asp
385                 390                 395                 400 cat tct gca act ttg gaa gaa tta gca gct tat gca tta gct aaa gat        1248
His Ser Ala Thr Leu Glu Glu Leu Ala Ala Tyr Ala Leu Ala Lys Asp
                405                 410                 415 aca gtt gct ttg cct ggt tcc ggt aga caa gaa tac tta gaa agt att        1296
Thr Val Ala Leu Pro Gly Ser Gly Arg Gln Glu Tyr Leu Glu Ser Ile
            420                 425                 430 att aac caa att ttg ttt caa taa                                        1320
Ile Asn Gln Ile Leu Phe Gln
        435

<210> SEQ ID NO 8
<211> LENGTH: 439
<212> TYPE: PRT
<213> ORGANISM: Unknown
<220> FEATURE:
<223> OTHER INFORMATION: Obtained from Intestinal Protist of
      Reticulitermes speratus
```

<400> SEQUENCE: 8

```
Met Ser Gln Ile Phe Lys Asp Ile Pro Val Ile Lys Tyr Glu Gly Pro
1               5                   10                  15
Ala Ser Lys Asn Pro Leu Ser Phe Lys Tyr Tyr Asp Ala Asn Lys Val
            20                  25                  30
Ile Asp Gly Lys Pro Met Lys Glu His Leu Arg Tyr Ala Met Ala Trp
        35                  40                  45
Trp His Asn Leu Cys Ala Thr Gly Gln Asp Met Phe Gly Pro Gly Thr
    50                  55                  60
Ala Asp Lys Ser Phe Gly Ser Lys Thr Val Gly Thr Met Glu His Ala
65                  70                  75                  80
His Ala Lys Val Asp Ala Gly Phe Glu Phe Met Ser Lys Leu Gly Val
                85                  90                  95
Glu Tyr Phe Cys Phe His Asp Ala Asp Leu Val Pro Glu Ala Asp Thr
            100                 105                 110
Leu Ser Glu Thr Asn Lys Arg Leu Asp Glu Ile Ala Glu His Ile Val
        115                 120                 125
Ala Lys Gln Lys Ala Thr Gly Ile Lys Cys Leu Trp Gly Thr Ala Asn
130                 135                 140
Leu Phe Ser Asn Pro Arg Phe Leu Asn Gly Ser Gly Ser Asn Ser
145                 150                 155                 160
Ala Asp Val Tyr Ala Tyr Ala Ala Gln Ile Lys Lys Ala Leu Asp
                165                 170                 175
Leu Thr Val Lys Phe Gly Gly Val Gly Tyr Val Phe Trp Gly Gly Arg
        180                 185                 190
Glu Gly Tyr Glu Thr Leu Leu Asn Thr Asp Val Lys Phe Glu Gln Glu
    195                 200                 205
Asn Ile Ala Asn Leu Met His Leu Ala Val Thr Tyr Gly Arg Ser Ile
210                 215                 220
Gly Phe Lys Gly Asp Phe Tyr Ile Glu Pro Lys Pro Lys Glu Pro Thr
225                 230                 235                 240
Lys His Gln Tyr Asp Phe Asp Ala Ala Thr Thr Ile Gly Phe Ile Arg
                245                 250                 255
Gln Tyr Gly Leu Glu Lys Asp Phe Lys Leu Asn Ile Glu Ala Asn His
            260                 265                 270
Ala Thr Leu Ala Gly His Thr Phe Gln His Asp Leu Arg Ile Ser Ala
        275                 280                 285
Ile Asn Gly Met Leu Gly Ser Val Asp Ala Asn Thr Gly Asp Pro Leu
    290                 295                 300
Leu Gly Trp Asp Thr Asp Glu Phe Pro Tyr Ser Val Tyr Asp Thr Thr
305                 310                 315                 320
Leu Ala Met Tyr Glu Ile Ile Lys Ala Gly Leu Thr Gly Gly Leu
                325                 330                 335
Asn Phe Asp Ser Lys Val Arg Arg Pro Ser Tyr Thr His Glu Asp Leu
            340                 345                 350
Phe Tyr Gly Phe Ile Leu Gly Met Asp Ser Phe Ala Leu Gly Leu Ile
        355                 360                 365
Lys Ala Lys Ala Leu Ile Ala Asp Gly Arg Leu Asp Ser Phe Val Lys
    370                 375                 380
Asp Arg Tyr Ala Ser Tyr Gly Ser Gly Ile Gly Ala Lys Ile Arg Asp
385                 390                 395                 400
His Ser Ala Thr Leu Glu Glu Leu Ala Ala Tyr Ala Leu Ala Lys Asp
```

```
                        405                 410                 415
Thr Val Ala Leu Pro Gly Ser Gly Arg Gln Glu Tyr Leu Glu Ser Ile
                420                 425                 430

Ile Asn Gln Ile Leu Phe Gln
        435

<210> SEQ ID NO 9
<211> LENGTH: 1803
<212> TYPE: DNA
<213> ORGANISM: Saccharomyces cerevisiae
<220> FEATURE:
<221> NAME/KEY: CDS
<222> LOCATION: (1)..(1803)

<400> SEQUENCE: 9 atg ttg tgt tca gta att cag aga cag aca aga gag gtt tcc aac aca    48
Met Leu Cys Ser Val Ile Gln Arg Gln Thr Arg Glu Val Ser Asn Thr
1               5                   10                  15 atg tct tta gac tca tac tat ctt ggg ttt gat ctt tcg acc caa caa    96
Met Ser Leu Asp Ser Tyr Tyr Leu Gly Phe Asp Leu Ser Thr Gln Gln
            20                  25                  30 ctg aaa tgt ctc gcc att aac cag gac cta aaa att gtc cat tca gaa   144
Leu Lys Cys Leu Ala Ile Asn Gln Asp Leu Lys Ile Val His Ser Glu
        35                  40                  45 aca gtg gaa ttt gaa aag gat ctt ccg cat tat cac aca aag aag ggt   192
Thr Val Glu Phe Glu Lys Asp Leu Pro His Tyr His Thr Lys Lys Gly
    50                  55                  60 gtc tat ata cac ggc gac act atc gaa tgt ccc gta gcc atg tgg tta   240
Val Tyr Ile His Gly Asp Thr Ile Glu Cys Pro Val Ala Met Trp Leu
65                  70                  75                  80 gag gct cta gat ctg gtt ctc tcg aaa tat cgc gag gct aaa ttt cca   288
Glu Ala Leu Asp Leu Val Leu Ser Lys Tyr Arg Glu Ala Lys Phe Pro
                85                  90                  95 ttg aac aaa gtt atg gcc gtc tca ggg tcc tgc cag cag cac ggg tct   336
Leu Asn Lys Val Met Ala Val Ser Gly Ser Cys Gln Gln His Gly Ser
            100                 105                 110 gtc tac tgg tcc tcc caa gcc gaa tct ctg tta gag caa ttg aat aag   384
Val Tyr Trp Ser Ser Gln Ala Glu Ser Leu Leu Glu Gln Leu Asn Lys
        115                 120                 125 aaa ccg gaa aaa gat tta ttg cac tac gtg agc tct gta gca ttt gca   432
Lys Pro Glu Lys Asp Leu Leu His Tyr Val Ser Ser Val Ala Phe Ala
    130                 135                 140 agg caa acc gcc ccc aat tgg caa gac cac agt act gca aag caa tgt   480
Arg Gln Thr Ala Pro Asn Trp Gln Asp His Ser Thr Ala Lys Gln Cys
145                 150                 155                 160 caa gag ttt gaa gag tgc ata ggt ggg cct gaa aaa atg gct caa tta   528
Gln Glu Phe Glu Glu Cys Ile Gly Gly Pro Glu Lys Met Ala Gln Leu
                165                 170                 175 aca ggg tcc aga gcc cat ttt aga ttt act ggt cct caa att ctg aaa   576
Thr Gly Ser Arg Ala His Phe Arg Phe Thr Gly Pro Gln Ile Leu Lys
            180                 185                 190 att gca caa tta gaa cca gaa gct tac gaa aaa aca aag acc att tct   624
Ile Ala Gln Leu Glu Pro Glu Ala Tyr Glu Lys Thr Lys Thr Ile Ser
        195                 200                 205 tta gtg tct aat ttt ttg act tct atc tta gtg ggc cat ctt gtt gaa   672
Leu Val Ser Asn Phe Leu Thr Ser Ile Leu Val Gly His Leu Val Glu
    210                 215                 220 tta gag gag gca gat gcc tgt ggt atg aac ctt tat gat ata cgt gaa   720
Leu Glu Glu Ala Asp Ala Cys Gly Met Asn Leu Tyr Asp Ile Arg Glu
225                 230                 235                 240
```

```
aga aaa ttc agt gat gag cta cta cat cta att gat agt tct tct aag    768
Arg Lys Phe Ser Asp Glu Leu Leu His Leu Ile Asp Ser Ser Ser Lys
            245                 250                 255 gat aaa act atc aga caa aaa tta atg aga gca ccc atg aaa aat ttg    816
Asp Lys Thr Ile Arg Gln Lys Leu Met Arg Ala Pro Met Lys Asn Leu
            260                 265                 270 ata gcg ggt acc atc tgt aaa tat ttt att gag aag tac ggt ttc aat    864
Ile Ala Gly Thr Ile Cys Lys Tyr Phe Ile Glu Lys Tyr Gly Phe Asn
            275                 280                 285 aca aac tgc aag gtc tct ccc atg act ggg gat aat tta gcc act ata    912
Thr Asn Cys Lys Val Ser Pro Met Thr Gly Asp Asn Leu Ala Thr Ile
            290                 295                 300 tgt tct tta ccc ctg cgg aag aat gac gtt ctc gtt tcc cta gga aca    960
Cys Ser Leu Pro Leu Arg Lys Asn Asp Val Leu Val Ser Leu Gly Thr
305             310                 315                 320 agt act aca gtt ctt ctg gtc acc gat aag tat cac ccc tct ccg aac   1008
Ser Thr Thr Val Leu Leu Val Thr Asp Lys Tyr His Pro Ser Pro Asn
                325                 330                 335 tat cat ctt ttc att cat cca act ctg cca aac cat tat atg ggt atg   1056
Tyr His Leu Phe Ile His Pro Thr Leu Pro Asn His Tyr Met Gly Met
                340                 345                 350 att tgt tat tgt aat ggt tct ttg gca agg gag agg ata aga gac gag   1104
Ile Cys Tyr Cys Asn Gly Ser Leu Ala Arg Glu Arg Ile Arg Asp Glu
            355                 360                 365 tta aac aaa gaa cgg gaa aat aat tat gag aag act aac gat tgg act   1152
Leu Asn Lys Glu Arg Glu Asn Asn Tyr Glu Lys Thr Asn Asp Trp Thr
370             375                 380 ctt ttt aat caa gct gtg cta gat gac tca gaa agt agt gaa aat gaa   1200
Leu Phe Asn Gln Ala Val Leu Asp Asp Ser Glu Ser Ser Glu Asn Glu
385                 390                 395                 400 tta ggt gta tat ttt cct ctg ggg gag atc gtt cct agc gta aaa gcc   1248
Leu Gly Val Tyr Phe Pro Leu Gly Glu Ile Val Pro Ser Val Lys Ala
                405                 410                 415 ata aac aaa agg gtt atc ttc aat cca aaa acg ggt atg att gaa aga   1296
Ile Asn Lys Arg Val Ile Phe Asn Pro Lys Thr Gly Met Ile Glu Arg
            420                 425                 430 gag gtg gcc aag ttc aaa gac aag agg cac gat gcc aaa aat att gta   1344
Glu Val Ala Lys Phe Lys Asp Lys Arg His Asp Ala Lys Asn Ile Val
            435                 440                 445 gaa tca cag gct tta agt tgc agg gta aga ata tct ccc ctg ctt tcg   1392
Glu Ser Gln Ala Leu Ser Cys Arg Val Arg Ile Ser Pro Leu Leu Ser
450                 455                 460 gat tca aac gca agc tca caa cag aga ctg aac gaa gat aca atc gtg   1440
Asp Ser Asn Ala Ser Ser Gln Gln Arg Leu Asn Glu Asp Thr Ile Val
465                 470                 475                 480 aag ttt gat tac gat gaa tct ccg ctg cgg gac tac cta aat aaa agg   1488
Lys Phe Asp Tyr Asp Glu Ser Pro Leu Arg Asp Tyr Leu Asn Lys Arg
                485                 490                 495 cca gaa agg act ttt ttt gta ggt ggg gct tct aaa aac gat gct att   1536
Pro Glu Arg Thr Phe Phe Val Gly Gly Ala Ser Lys Asn Asp Ala Ile
            500                 505                 510 gtg aag aag ttt gct caa gtc att ggt gct aca aag ggt aat ttt agg   1584
Val Lys Lys Phe Ala Gln Val Ile Gly Ala Thr Lys Gly Asn Phe Arg
            515                 520                 525 cta gaa aca cca aac tca tgt gcc ctt ggt ggt tgt tat aag gcc atg   1632
Leu Glu Thr Pro Asn Ser Cys Ala Leu Gly Gly Cys Tyr Lys Ala Met
            530                 535                 540 tgg tca ttg tta tat gac tct aat aaa att gca gtt cct ttt gat aaa   1680
Trp Ser Leu Leu Tyr Asp Ser Asn Lys Ile Ala Val Pro Phe Asp Lys
545                 550                 555                 560
```

```
ttt ctg aat gac aat ttt cca tgg cat gta atg gaa agc ata tcc gat    1728
Phe Leu Asn Asp Asn Phe Pro Trp His Val Met Glu Ser Ile Ser Asp
                565                 570                 575 gtg gat aat gaa aat tgg gat cgc tat aat tcc aag att gtc ccc tta    1776
Val Asp Asn Glu Asn Trp Asp Arg Tyr Asn Ser Lys Ile Val Pro Leu
            580                 585                 590 agc gaa ctg gaa aag act ctc atc taa                                1803
Ser Glu Leu Glu Lys Thr Leu Ile
        595                 600
```

<210> SEQ ID NO 10
<211> LENGTH: 600
<212> TYPE: PRT
<213> ORGANISM: Saccharomyces cerevisiae

<400> SEQUENCE: 10

```
Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Val Gly His Leu Val Glu
    210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Lys
                245                 250                 255

Asp Lys Thr Ile Arg Gln Lys Leu Met Arg Ala Pro Met Lys Asn Leu
            260                 265                 270

Ile Ala Gly Thr Ile Cys Lys Tyr Phe Ile Glu Lys Tyr Gly Phe Asn
        275                 280                 285

Thr Asn Cys Lys Val Ser Pro Met Thr Gly Asp Asn Leu Ala Thr Ile
    290                 295                 300

Cys Ser Leu Pro Leu Arg Lys Asn Asp Val Leu Val Ser Leu Gly Thr
```

```
            305                 310                 315                 320
        Ser Thr Thr Val Leu Leu Val Thr Asp Lys Tyr His Pro Ser Pro Asn
                    325                 330                 335

Tyr His Leu Phe Ile His Pro Thr Leu Pro Asn His Tyr Met Gly Met
                    340                 345                 350

Ile Cys Tyr Cys Asn Gly Ser Leu Ala Arg Glu Arg Ile Arg Asp Glu
                    355                 360                 365

Leu Asn Lys Glu Arg Glu Asn Asn Tyr Glu Lys Thr Asn Asp Trp Thr
        370                 375                 380

Leu Phe Asn Gln Ala Val Leu Asp Asp Ser Glu Ser Ser Glu Asn Glu
        385                 390                 395                 400

Leu Gly Val Tyr Phe Pro Leu Gly Glu Ile Val Pro Ser Val Lys Ala
                    405                 410                 415

Ile Asn Lys Arg Val Ile Phe Asn Pro Lys Thr Gly Met Ile Glu Arg
                    420                 425                 430

Glu Val Ala Lys Phe Lys Asp Lys Arg His Asp Ala Lys Asn Ile Val
                    435                 440                 445

Glu Ser Gln Ala Leu Ser Cys Arg Val Arg Ile Ser Pro Leu Leu Ser
        450                 455                 460

Asp Ser Asn Ala Ser Ser Gln Gln Arg Leu Asn Glu Asp Thr Ile Val
        465                 470                 475                 480

Lys Phe Asp Tyr Asp Glu Ser Pro Leu Arg Asp Tyr Leu Asn Lys Arg
                    485                 490                 495

Pro Glu Arg Thr Phe Phe Val Gly Gly Ala Ser Lys Asn Asp Ala Ile
                    500                 505                 510

Val Lys Lys Phe Ala Gln Val Ile Gly Ala Thr Lys Gly Asn Phe Arg
                    515                 520                 525

Leu Glu Thr Pro Asn Ser Cys Ala Leu Gly Gly Cys Tyr Lys Ala Met
                    530                 535                 540

Trp Ser Leu Leu Tyr Asp Ser Asn Lys Ile Ala Val Pro Phe Asp Lys
        545                 550                 555                 560

Phe Leu Asn Asp Asn Phe Pro Trp His Val Met Glu Ser Ile Ser Asp
                    565                 570                 575

Val Asp Asn Glu Asn Trp Asp Arg Tyr Asn Ser Lys Ile Val Pro Leu
                    580                 585                 590

Ser Glu Leu Glu Lys Thr Leu Ile
                    595                 600

<210> SEQ ID NO 11
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 11
ggaaattttt taaagcttcc cttttacagt gcttc                              35

<210> SEQ ID NO 12
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 12
aaaaatttga gacattttgt tttgtgtgta aatttagtga ag                      42
```

<210> SEQ ID NO 13
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 13
atgtctcaaa tttttaagga tatcccag                                              28

<210> SEQ ID NO 14
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 14
ggggcctgtc ttaagttatt gaaacaaaat ttggttaata atactttc                        48

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 15
cttaagacag gcccctttc ctttg                                                  25

<210> SEQ ID NO 16
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 16
taacattcaa cgctactgca ggaattcgat atc                                        33

<210> SEQ ID NO 17
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 17
tagcgttgaa tgttagcgtc aacaac                                                26

<210> SEQ ID NO 18
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 18
tactgaacac aacattttgt ttgtttatgt gtgtttattc g                               41

<210> SEQ ID NO 19
<211> LENGTH: 27
<212> TYPE: DNA
<213> ORGANISM: Artificial Sequence
<220> FEATURE:

```
<223> OTHER INFORMATION: Synthetic oligonucleotide primer

<400> SEQUENCE: 19
atgttgtgtt cagtaattca gagacag                                27

<210> SEQ ID NO 20
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 20
aaataatcgg tgtcattaga tgagagtctt ttccagttc                   39

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 21
tgacaccgat tatttaaagc tgcag                                  25

<210> SEQ ID NO 22
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 22
agagcgcgcc tcgttc                                            16

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 23
tgggaatatt accgctcgaa g                                      21

<210> SEQ ID NO 24
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 24
ctttaaaaaa tttccaattt tcctttacg                              29

<210> SEQ ID NO 25
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 25
aacgaggcgc gctcttccag ccagtaaaat ccatac                      36
```

```
<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 26 aaggggggaag gtgtggaatc                                              20

<210> SEQ ID NO 27
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 27
tagcgttgaa tgttagcgtc aacaac                                        26

<210> SEQ ID NO 28
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 28
tttgtttgtt tatgtgtgtt tattcgaaac taagttcttg g                       41

<210> SEQ ID NO 29
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 29
atgctaagaa acattttggt gagaag                                        26

<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 30
agtcagtctg gtttgtatct tg                                            22

<210> SEQ ID NO 31
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 31
atggcaaact acttcaacac tttgaatttg                                    30

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide primer
```

<400> SEQUENCE: 32
ttaacctgca acagcgattc                                                   20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 33
ccaactgtcc tcacgctgac                                                   20

<210> SEQ ID NO 34
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 34
cttatttaga agtgtcaaca acgtatctac c                                      31

<210> SEQ ID NO 35
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 35
gcggatctct tatgtcttta cgatttatag ttttc                                  35

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 36
gagggttggg cattcatcag                                                   20

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 37
cttaagacag gcccctttc ctttg                                              25

<210> SEQ ID NO 38
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 38
ctgcaggaat tcgatatcaa gcttatc                                           27

<210> SEQ ID NO 39
<211> LENGTH: 40

```
<212> TYPE: DNA
<213> ORGANISM: Artificial Sequence
<220> FEATURE:
<223> OTHER INFORMATION: Synthetic oligonucleotide primer

<400> SEQUENCE: 39
acgacattac tatatatata ataggaag catttaatag                              40

<210> SEQ ID NO 40
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 40
gacataagag atccgcagg                                                   19

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 41
aaacggccag tagccaagac                                                  20

<210> SEQ ID NO 42
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 42
actccaagct gcctttgtgt gc                                               22

<210> SEQ ID NO 43
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 43
agaggaaaat aatatcaagt gctggaaac                                        29

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 44
ccggaggctt tcaattgttc                                                  20

<210> SEQ ID NO 45
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 45
```
cttaagacag gcccctttc ctttg                                    25

<210> SEQ ID NO 46
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 46
atatagtaat gtcgtctgca ggaattcgat atcaag                       36

<210> SEQ ID NO 47
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 47
acgacattac tatatatata atataggaag catttaatag                   40

<210> SEQ ID NO 48
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 48
acataagaga tccgcaggca agtgcacaaa caatac                       36

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 49
ccaactgtcc tcacgctgac                                         20

<210> SEQ ID NO 50
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 50
ggggcctgtc ttaagcttat ttagaagtgt caacaacg                     38

<210> SEQ ID NO 51
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 51
gcggatctct tatgtcttta cgatttatag ttttc                        35

<210> SEQ ID NO 52
<211> LENGTH: 20
<212> TYPE: DNA
<213> ORGANISM: Artificial Sequence

```
<220> FEATURE:
<223> OTHER INFORMATION: Synthetic oligonucleotide primer

<400> SEQUENCE: 52
gagggttggg cattcatcag                                             20
```

RECOMBINANT YEAST AND METHOD FOR PRODUCING ETHANOL USING THE SAME

CROSS REFERENCE TO RELATED APPLICATIONS

This application is a National Stage of International Application No. PCT/JP2014/003069 filed Jun. 9, 2014, claiming priority based on Japanese Patent Application No. 2013-124755, filed Jun. 13, 2013, the contents of all of which are incorporated herein by reference in their entirety.

TECHNICAL FIELD

The present invention relates to a recombinant yeast having xylose-metabolizing ability and a method for producing ethanol using the same.

BACKGROUND ART

Major saccharides contained in lignocellulose are glucose that constitutes cellulose and xylose that constitutes hemicellulose. By chemically or enzymatically degrading lignocellulose, a saccharified composition mainly composed of such a monosaccharide can be obtained. Production of useful materials from lignocellulose at the industrial level necessitates microorganisms that are capable of effective utilization of saccharides contained in such saccharified compositions and fermentation of such useful substances with high yield and high productivity.

In general, yeasts with high ethanol fermentation ability, such as Saccharomyces cerevisiae, are capable of utilizing glucose, mannose, or galactose, although such yeasts are not capable of utilizing xylose. In order to perform fermentation using lignocellulose as a starting material with high efficiency, accordingly, it is necessary that such yeasts be modified to be capable of using xylose.

For example, production of recombinant *S. cerevisiae* capable of xylose utilization has been attempted (Patent Literature 1 and 2; Non-Patent Literature 1). Patent Literature 1 and Non-Patent Literature 1 each report improvement in ethanol yield and xylose utilization of a yeast to which xylose assimilability has been imparted through introduction of genes encoding xylose reductase (XR) and xylitol dehydrogenase (XDH) from different microorganisms. Such literature reports that the phosphoketolase (PK) pathway is potentiated and NADH is consumed by acetaldehyde dehydrogenase, in order to consume excessive NADH generated by introduction of a xylose assimilation pathway caused by XR and XDH in the subsequent reaction.

Patent Literature 2 reports the use of xylose isomerase (XI), which is an isomerase that converts xylose into xylulose. When XI is used, excessive NADH is not generated. That is, the glycolytic pentose phosphate pathway (PPP) is used without any processing, and the phosphoketolase pathway is not potentiated in the technique according to Patent Literature 2.

While NADH may be excessively consumed as a result of introduction of the acetaldehyde dehydrogenase gene into a xylose-assimilating yeast into which the XI gene had been introduced, the improvement of xylose assimilation as a result of introduction of such gene has also been reported (Patent Literature 3).

CITATION LIST

Patent Literature

{PTL 1}
WO 2003/078643

{PTL 2}
JP 2005-514951 A
{PTL 3}
JP 2010-239925 A

Non Patent Literature

{NPL 1}
Sonderegger M, Schumperli M, Sauer U. 2004, Metabolic engineering of a phosphoketolase pathway for pentose catabolism in Saccharomyces cerevisiae, Appl. Environ. Microbiol., 70 (5): 2892-2897

SUMMARY OF INVENTION

Technical Problem

However, the xylose-assimilating yeast into which the XI gene had been introduced was not sufficient in terms of ethanol fermentation ability; that is, such strain was not sufficient in terms of ethanol production efficiency. Under the above circumstances, it is an object of the present invention to provide a xylose-assimilating yeast that is particularly excellent in terms of xylose assimilation ability and ethanol fermentation ability. It is another object of the present invention to provide a method for producing ethanol that results in an excellent ethanol yield with the use of such yeast.

Solution to Problem

The present inventors have conducted concentrated studies in order to attain the above objects. As a result, they discovered that xylose assimilation ability and ethanol yield could be improved by decreasing the amount of NADH produced by an enzymatic reaction involving acetohydroxy acid reductoisomerase in a yeast having xylose metabolizing ability. This has led to the completion of the present invention.

The present invention is as follows.

(1) A recombinant yeast into which the xylose isomerase gene has been introduced, wherein a production of NADH as a result of the enzymatic reaction of acetohydroxy acid reductoisomerase is lowered.

(2) The recombinant yeast according to (1), wherein activity of endogenous acetohydroxy acid reductoisomerase is lowered.

(3) The recombinant yeast according to (1), wherein the expression level of the endogenous gene encoding acetohydroxy acid reductoisomerase is lowered.

(4) The recombinant yeast according to (3), wherein the endogenous gene is disrupted.

(5) The recombinant yeast according to (4), wherein the endogenous genes are hetero-disrupted.

(6) The recombinant yeast according to (1) into which a gene encoding mutant acetohydroxy acid reductoisomerase with lowered $NAD^+$ dependence and enhanced $NADP^+$ dependence is introduced.

(7) The recombinant yeast according to (3), wherein the endogenous gene encoding acetohydroxy acid reductoisomerase encodes the protein (a) or (b) below:

(a) the protein comprising the amino acid sequence as shown in SEQ ID NO: 2; or (b) the protein comprising an amino acid sequence having 70% or higher identity with the amino acid sequence as shown in SEQ ID NO: 2 and having enzymatic activity of converting 2-acetolactate and NAD⁺ into 2,3-dihydroxy-isovalerate and NADH, respectively.

(8) The recombinant yeast according to (6), wherein the gene encoding mutant acetohydroxy acid reductoisomerase encodes the protein (a) or (b) below:

(a) the protein comprising the amino acid sequence as shown in SEQ ID NO: 4 or 6; or (b) the protein comprising an amino acid sequence having 70% or higher identity with the amino acid sequence as shown in SEQ ID NO: 4 or 6 and having enzymatic activity of converting 2-acetolactate and NADP⁺ into 2,3-dihydroxy-isovalerate and NADPH, respectively.

(9) The recombinant yeast according to (1), wherein the xylose isomerase gene encodes the protein (a) or (b) below:

(a) the protein comprising the amino acid sequence as shown in SEQ ID NO: 8; or (b) the protein comprising an amino acid sequence having 70% or higher identity with the amino acid sequence as shown in SEQ ID NO: 8 and having enzymatic activity of converting xylose into xylulose.

(10) A method for producing ethanol comprising a step of culturing the recombinant yeast according to any of (1) to (9) in a xylose-containing medium to perform ethanol fermentation.

Advantageous Effects of Invention

The recombinant yeast of the present invention is excellent in terms of the ability to assimilate xylose in a medium and efficiency for producing ethanol from xylose. With the use of the recombinant yeast of the present invention, accordingly, the ethanol yield in a xylose-containing medium can be remarkably improved.

According to the method for producing ethanol of the present invention, efficiency for ethanol fermentation using xylose in a medium as a saccharide source can be maintained at a high level, and an excellent ethanol yield can be achieved.

DESCRIPTION OF EMBODIMENTS

Hereafter, the present invention is described in greater detail with reference to the drawings and the examples.

<Recombinant Yeast>

The recombinant yeast of the present invention is obtained by introducing the xylose isomerase gene, in which a production of NADH (i.e., the reduced nicotinamide adenine dinucleotide) as a result of the enzymatic reaction of acetohydroxy acid reductoisomerase is lowered.

The recombinant yeast into which the xylose isomerase gene has been introduced is a recombinant yeast in which the xylose isomerase gene functions. When the xylose isomerase gene functions, the xylose isomerase gene that has been introduced is transcribed and translated, so as to express the xylose isomerase having enzymatic activity.

The term "the recombinant yeast into which the xylose isomerase gene has been introduced" refers to any of the following: a recombinant yeast that has acquired xylose-metabolizing ability as a result of introduction of a xylose isomerase gene into a yeast that does not inherently have xylose-metabolizing ability; a recombinant yeast that has acquired xylose-metabolizing ability as a result of introduction of a xylose isomerase gene and another xylose metabolism-associated gene into a yeast that does not inherently have xylose-metabolizing ability; and a recombinant yeast that has enhanced xylose-metabolizing ability as a result of introduction of a xylose isomerase gene into a yeast that inherently has xylose-metabolizing ability.

The recombinant yeast of the present invention is capable of assimilating xylose contained in a medium to produce ethanol. Xylose contained in a medium may be obtained by saccharification of xylan or hemicellulose comprising xylose as a constituent sugar. Alternatively, it may be supplied to a medium as a result of saccharification of xylan or hemicellulose contained in a medium by a saccharification enzyme. The latter case is the so-called "simultaneous saccharification and fermentation system."

Figure 1:
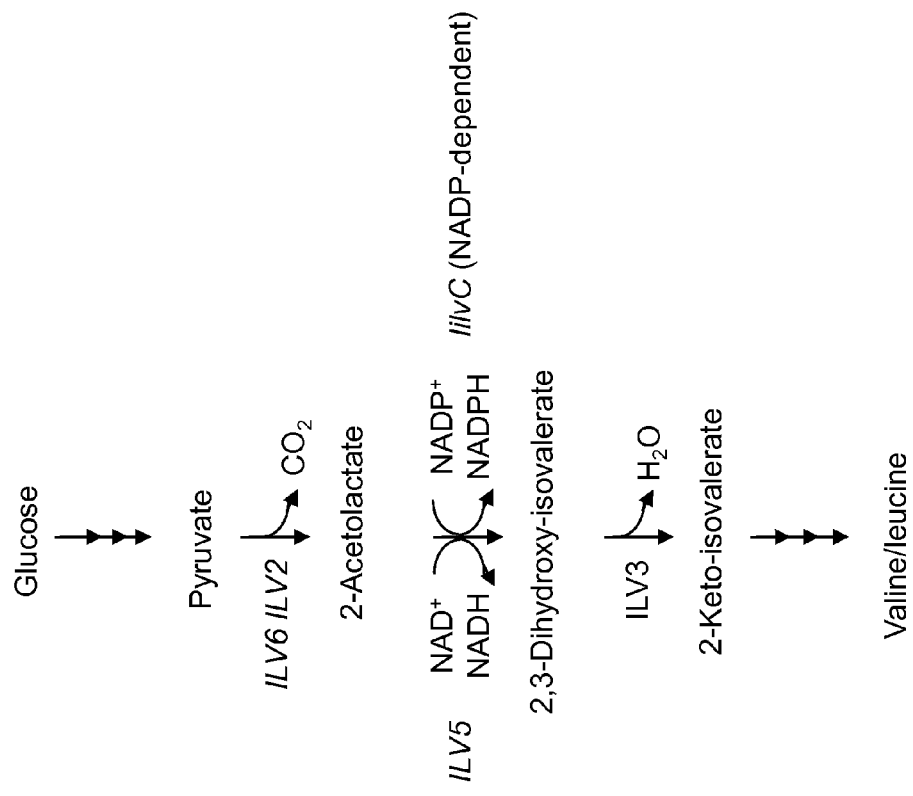
FIG. 1 is a characteristic diagram showing part of the pathway of valine/leucine biosynthesis.

In the recombinant yeast of the present invention, the amount of NADH produced as a result of the enzymatic reaction of acetohydroxy acid reductoisomerase is lowered. As shown in FIG. 1, acetohydroxy acid reductoisomerase is an enzyme having activity of converting 2-acetolactate and NAD⁺ into 2,3-dihydroxy-isovalerate and NADH, respectively, in the pathway of valine/leucine biosynthesis (i.e., the enzyme indicated as "ILV5" in FIG. 1).

In order to lower the amount of NADH produced as a result of the enzymatic reaction of acetohydroxy acid reductoisomerase, for example, activity of acetohydroxy acid reductoisomerase inherent in the recombinant yeast may be lowered, or the expression level of acetohydroxy acid reductoisomerase gene inherent in the recombinant yeast may be lowered. Alternatively, a mutant acetohydroxy acid reductoisomerase gene having lowered NAD⁺ dependence and enhanced NADP⁺ dependence may be introduced. That is, expression of mutant acetohydroxy acid reductoisomerase encoded by the mutant acetohydroxy acid reductoisomerase gene leads to relatively-lowering in activity of endogenous acetohydroxy acid reductoisomerase. Thus, the amount of NADH produced by endogenous acetohydroxy acid reductoisomerase is decreased, and the amount of NADPH (reduced nicotinamide adenine dinucleotide phosphate) produced by mutant acetohydroxy acid reductoisomerase is increased as a consequence. In FIG. 1, mutant acetohydroxy acid reductoisomerase is indicated as "IilvC" (NADP-dependent).

In order to lower the activity level of acetohydroxy acid reductoisomerase inherent in the recombinant yeast, for example, a substance that inhibits activity of acetohydroxy acid reductoisomerase or an antibody that neutralizes activity of acetohydroxy acid reductoisomerase may be allowed to coexist with acetohydroxy acid reductoisomerase. In order to lower the expression level of acetohydroxy acid reductoisomerase gene endogenous to the recombinant yeast, for example, a promoter of the endogenous gene may be modified, or such gene may be deleted or disrupted. Examples of techniques for suppressing gene expression include the transposon technique, the transgene technique, the post-transcriptional gene silencing technique, the RNAi technique, the nonsense mediated decay (NMD) technique, the ribozyme technique, the anti-sense technique, the miRNA (micro-RNA) technique, and the siRNA (small interfering RNA) technique. It is particularly preferable that acetohydroxy acid reductoisomerase gene endogenous to the recombinant yeast be deleted or disrupted and that one of the alleles be deleted or disrupted.

The term "endogenous acetohydroxy acid reductoisomerase gene" refers to a gene that inherently exists in the recombinant yeast of the present invention and encodes a protein having enzymatic activity of converting 2-acetolactate and $NAD^+$ into 2,3-dihydroxy-isovalerate and NADH, respectively. Thus, the nucleotide sequence constituting endogenous acetohydroxy acid reductoisomerase gene is not particularly limited.

For example, SEQ ID NOs: 1 and 2 show the nucleotide sequence of acetohydroxy acid reductoisomerase gene inherent in *Saccharomyces cerevisiae* and the amino acid sequence of acetohydroxy acid reductoisomerase encoded by such gene, respectively.

The acetohydroxy acid reductoisomerase gene is not limited to the gene identified by SEQ ID NOs: 1 and 2. It may be a paralogous gene or a homologous gene in the narrow sense having different nucleotide and amino acid sequences.

The acetohydroxy acid reductoisomerase gene is not limited to the gene identified by SEQ ID NOs: 1 and 2. For example, it may be a gene comprising an amino acid sequence having 70% or higher, preferably 80% or higher, more preferably 90% or higher, and most preferably 95% or higher sequence similarity or identity with the amino acid sequence as shown in SEQ ID NO: 2 and encoding a protein having enzymatic activity of converting 2-acetolactate and $NAD^+$ into 2,3-dihydroxy-isovalerate and NADH, respectively. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, acetohydroxy acid reductoisomerase gene is not limited to the gene identified by SEQ ID NOs: 1 and 2. For example, it may be a gene comprising an amino acid sequence derived from the amino acid sequence as shown in SEQ ID NO: 2 by substitution, deletion, insertion, or addition of one or several amino acids and encoding a protein having enzymatic activity of converting 2-acetolactate and $NAD^+$ into 2,3-dihydroxy-isovalerate and NADH, respectively. The term "several" used herein refers to, for example, 2 to 30, preferably 2 to 20, more preferably 2 to 10, and most preferably 2 to 5.

Furthermore, acetohydroxy acid reductoisomerase gene is not limited to the gene identified by SEQ ID NOs: 1 and 2. For example, it may be a gene hybridizing under stringent conditions to the full-length sequence or a partial sequence of a complementary strand of DNA comprising the nucleotide sequence as shown in SEQ ID NO: 1 and encoding a protein having enzymatic activity of converting 2-acetolactate and $NAD^+$ into 2,3-dihydroxy-isovalerate and NADH, respectively. Under "stringent conditions," so-called specific hybrids are formed, but non-specific hybrids are not formed. Such conditions can be adequately determined with reference to, for example, Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42 degrees C. to 68 degrees C. and preferably 42 degrees C. to 65 degrees C., for example. Further specifically, the sodium concentration is 5×SSC (83 mM NaCl, 83 mM sodium citrate), and the temperature is 42 degrees C.

As described above, whether or not a gene comprising a nucleotide sequence that differs from the sequence shown in SEQ ID NO: 1 or a gene encoding an amino acid sequence that differs from the sequence shown in SEQ ID NO: 2 would function as acetohydroxy acid reductoisomerase gene may be determined by, for example, preparing an expression vector comprising the gene of interest incorporated into an adequate site between a promoter and a terminator, transforming an *E. coli* host using such expression vector, and assaying acetohydroxy acid reductoisomerase activity of the protein expressed. The term "acetohydroxy acid reductoisomerase activity" refers to activity of converting 2-acetolactate and $NAD^+$ into 2,3-dihydroxy-isovalerate and NADH, respectively. Thus, acetohydroxy acid reductoisomerase activity can be evaluated by preparing a solution containing 2-acetolactate and $NAD^+$ as substrates, allowing the target protein to react at an adequate temperature, and measuring the amount of 2-acetolactate and $NAD^+$ that had decreased and/or the amount of 2,3-dihydroxy-isovalerate and NADH that had been produced.

The mutant acetohydroxy acid reductoisomerase gene with lowered $NAD^+$ dependence and enhanced $NADP^+$ dependence is not particularly limited. For example, such gene may encode a mutant enzyme prepared by modifying amino acid residues constituting the NADPH-binding site in wild-type acetohydroxy acid reductoisomerase, so as to lower $NAD^+$ dependence and enhance $NADP^+$ dependence. The gene disclosed in, for example, U.S. Pat. No. 8,097,440 or Arch. Biochem. Biophys., 338, pp. 83-89, 1997 can be adequately used as such mutant acetohydroxy acid reductoisomerase gene.

Specifically, the mutations R68D, K69L, K75V, and R76D may be introduced into the *E. coli*-derived acetohydroxy acid reductoisomerase, so as to lower $NAD^+$ dependence and enhance $NADP^+$ dependence. Also, the mutations A71S, R76D, S78D, Q110V, D146G, and G185R may be introduced into the *E. coli*-derived acetohydroxy acid reductoisomerase, so as to lower $NAD^+$ dependence and enhance $NADP^+$ dependence.

More specifically, the nucleotide sequence of the *E. coli*-derived mutant acetohydroxy acid reductoisomerase gene resulting from introduction of the mutations R68D, K69L, K75V, and R76D is shown in SEQ ID NO: 3, and the amino acid sequence of mutant acetohydroxy acid reductoisomerase encoded by such gene is shown in SEQ ID NO: 4. Also, the nucleotide sequence of the *E. coli*-derived mutant acetohydroxy acid reductoisomerase gene resulting from introduction of the mutations A71S, R76D, S78D, Q110V, D146G, and G185R is shown in SEQ ID NO: 5, and the amino acid sequence of mutant acetohydroxy acid reductoisomerase encoded by such gene is shown in SEQ ID NO: 6.

The mutant acetohydroxy acid reductoisomerase gene is not limited to the gene identified by SEQ ID NOs: 3 to 6. For example, it may be a gene comprising an amino acid sequence having 70% or higher, preferably 80% or higher, more preferably 90% or higher, and most preferably 95% or higher sequence similarity or identity with the amino acid sequence as shown in SEQ ID NO: 4 or 6 and encoding a protein having enzymatic activity of converting 2-acetolactate and NADP$^+$ into 2,3-dihydroxy-isovalerate and NADPH, respectively. An amino acid sequence having a given level of sequence similarity or identity with the amino acid sequence as shown in SEQ ID NO: 4 is required to conserve the mutations R68D, K69L, K75V, and R76D. Also, an amino acid sequence having a given level of sequence similarity or identity with the amino acid sequence as shown in SEQ ID NO: 6 is required to conserve the mutations A71S, R76D, S78D, Q110V, D146G, and G185R. The degree of sequence similarity or identity can be determined using the BLASTN or BLASTX Program equipped with the BLAST algorithm (at default settings).

The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the mutant acetohydroxy acid reductoisomerase gene is not limited to the gene identified by SEQ ID NOs: 3 to 6. For example, it may be a gene comprising an amino acid sequence derived from the amino acid sequence as shown in SEQ ID NO: 4 or 6 by substitution, deletion, insertion, or addition of one or several amino acids and encoding a protein having enzymatic activity of converting 2-acetolactate and NADP$^+$ into 2,3-dihydroxy-isovalerate and NADPH, respectively. The term "several" used herein refers to, for example, 2 to 30, preferably 2 to 20, more preferably 2 to 10, and most preferably 2 to 5. An amino acid sequence derived from the amino acid sequence as shown in SEQ ID NO: 4 by substitution, deletion, insertion, or addition of a given number of amino acids is required to conserve the mutations R68D, K69L, K75V, and R76D. Also, an amino acid sequence derived from the amino acid sequence as shown in SEQ ID NO: 6 by substitution, deletion, insertion, or addition of a given number of amino acids is required to conserve the mutations A71S, R76D, S78D, Q110V, D146G, and G185R.

Furthermore, the mutant acetohydroxy acid reductoisomerase gene is not limited to the gene identified by SEQ ID NOs: 3 to 6. For example, it may be a gene hybridizing under stringent conditions to the full-length sequence or a partial sequence of a complementary strand of DNA comprising the nucleotide sequence as shown in SEQ ID NO: 3 or 5 and encoding a protein having enzymatic activity of converting 2-acetolactate and NADP$^+$ into 2,3-dihydroxy-isovalerate and NADPH, respectively. Under "stringent conditions," so-called specific hybrids are formed, but non-specific hybrids are not formed. Such conditions can be adequately determined with reference to, for example, Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization.

Under stringent conditions, more specifically, the sodium concentration is 25 to 500 mM and preferably 25 to 300 mM, and the temperature is 42 degrees C. to 68 degrees C. and preferably 42 degrees C. to 65 degrees C., for example. Further specifically, the sodium concentration is 5×SSC (83 mM NaCl, 83 mM sodium citrate), and the temperature is 42 degrees C. A polynucleotide hybridizing under stringent conditions to the full-length sequence or a partial sequence of a complementary strand of DNA comprising the nucleotide sequence as shown in SEQ ID NO: 3 is required to encode an amino acid sequence that has conserved the mutations R68D, K69L, K75V, and R76D. Also, a polynucleotide hybridizing under stringent conditions to the full-length sequence or a partial sequence of a complementary strand of DNA comprising the nucleotide sequence as shown in SEQ ID NO: 6 is required to encode an amino acid sequence that has conserved the mutations A71S, R76D, S78D, Q110V, D146G, and G185R.

As described above, whether or not a gene comprising a nucleotide sequence that differs from the sequence shown in SEQ ID NO: 3 or 5 or a gene encoding an amino acid sequence that differs from the sequence shown in SEQ ID NO: 4 or 6 would function as the mutant acetohydroxy acid reductoisomerase gene may be determined by, for example, preparing an expression vector comprising the gene of interest incorporated into an adequate site between a promoter and a terminator, transforming an *E. coli* host using such expression vector, and assaying mutant acetohydroxy acid reductoisomerase activity of the protein expressed. The term "mutant acetohydroxy acid reductoisomerase activity" refers to activity of converting 2-acetolactate and NADP$^+$ into 2,3-dihydroxy-isovalerate and NADPH, respectively. Thus, mutant acetohydroxy acid reductoisomerase activity can be evaluated by preparing a solution containing 2-acetolactate and NADP$^+$ as substrates, allowing the target protein to react at an adequate temperature, and measuring the amount of 2-acetolactate and NADP$^+$ that had decreased and/or the amount of 2,3-dihydroxy-isovalerate and NADPH that had been produced.

As described above, the recombinant yeast of the present invention comprises a xylose isomerase gene that has been introduced thereinto. The xylose isomerase gene (the XI gene) is not particularly limited, and a gene originating from any organism species may be used. For example, a plurality of the xylose isomerase genes derived from the intestinal protozoa of termites disclosed in JP 2011-147445 A can be used without particular limitation. Examples of the xylose isomerase genes that can be used include a gene derived from the anaerobic fungus *Piromyces* sp. strain E2 (JP 2005-514951 A), a gene derived from the anaerobic fungus *Cyllamyces aberensis*, a gene derived from a bacterial strain (i.e., *Bacteroides thetaiotaomicron*), a gene derived from another bacterial strain (i.e., *Clostridium phytofermentans*), and a gene derived from the *Streptomyces murinus* cluster.

Specifically, use of a xylose isomerase gene derived from the intestinal protozoa of *Reticulitermes speratus* as the xylose isomerase gene is preferable. The nucleotide sequence of the coding region of the xylose isomerase gene derived from the intestinal protozoa of *Reticulitermes speratus* and the amino acid sequence of a protein encoded by such gene are shown in SEQ ID NOs: 7 and 8, respectively.

The xylose isomerase gene is not limited to the gene identified by SEQ ID NOs: 7 and 8. It may be a paralogous gene or a homologous gene in the narrow sense having different nucleotide and amino acid sequences.

The xylose isomerase gene is not limited to the gene identified by SEQ ID NOs: 7 and 8. For example, it may be a gene comprising an amino acid sequence having 70% or higher, preferably 80% or higher, more preferably 90% or higher, and most preferably 95% or higher sequence similarity or identity with the amino acid sequence as shown in SEQ ID NO: 8 and encoding a protein having xylose isomerase activity. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the xylose isomerase gene is not limited to the gene identified by SEQ ID NOs: 7 and 8. For example, it may be a gene comprising an amino acid sequence derived from the amino acid sequence as shown in SEQ ID NO: 8 by substitution, deletion, insertion, or addition of one or several amino acids and encoding a protein having xylose isomerase activity. The term "several" used herein refers to, for example, 2 to 30, preferably 2 to 20, more preferably 2 to 10, and most preferably 2 to 5.

Furthermore, the xylose isomerase gene is not limited to the gene identified by SEQ ID NOs: 7 and 8. For example, it may be a gene hybridizing under stringent conditions to the full-length sequence or a partial sequence of a complementary strand of DNA comprising the nucleotide sequence as shown in SEQ ID NO: 7 and encoding a protein having xylose isomerase activity. Under "stringent conditions," so-called specific hybrids are formed, but non-specific hybrids are not formed. Such conditions can be adequately determined with reference to, for example, Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42 degrees C. to 68 degrees C. and preferably 42 degrees C. to 65 degrees C., for example. Further specifically, the sodium concentration is 5×SSC (83 mM NaCl, 83 mM sodium citrate), and the temperature is 42 degrees C.

As described above, whether or not a gene comprising a nucleotide sequence that differs from the sequence shown in SEQ ID NO: 7 or a gene encoding an amino acid sequence that differs from the sequence shown in SEQ ID NO: 8 would function as the xylose isomerase gene may be determined by, for example, preparing an expression vector comprising the gene of interest incorporated into an adequate site between a promoter and a terminator, transforming an *E. coli* host using such expression vector, and assaying xylose isomerase activity of the protein expressed. The term "xylose isomerase activity" refers to activity of isomerizing xylose into xylulose. Thus, xylose isomerase activity can be evaluated by preparing a solution containing xylose as a substrate, allowing the target protein to react at an adequate temperature, and measuring the amount of xylose that had decreased and/or the amount of xylulose that had been produced.

As described above, another xylose metabolism-associated gene may be introduced into the recombinant yeast of the present invention, in addition to the xylose isomerase gene. The xylose metabolism-associated gene other than the xylose isomerase gene may be the xylose reductase gene encoding xylose reductase that converts xylose into xylitol, the xylitol dehydrogenase gene encoding xylitol dehydrogenase that converts xylitol into xylulose, or the xylulokinase gene encoding the xylulokinase that phosphorylates xylulose to produce xylulose 5-phosphate. Xylulose 5-phosphate produced by xylulokinase is metabolized by the pentose phosphate pathway.

More specific examples of xylose metabolism-associated genes include, but are not particularly limited to, a xylose reductase gene and a xylitol dehydrogenase gene derived from *Pichia stipitis* and a xylulokinase gene derived from *Saccharomyces cerevisiae* (see Eliasson A. et al., Appl. Environ. Microbiol., 66: 3381-3386; and Toivari M. N. et al., Metab. Eng., 3: 236-249). In addition, xylose reductase genes derived from *Candida tropicalis* and *Candida prapsilosis*, xylitol dehydrogenase genes derived from *Candida tropicalis* and *Candida prapsilosis*, and a xylulokinase gene derived from *Pichia stipitis* can be used.

It is particularly preferable that the recombinant yeast of the present invention comprise axylulokinase gene that has been introduced thereinto, in addition to the xylose isomerase gene. Xylulokinase is involved in a reaction that generates xylulose 5-phosphate with the use of xylulose generated by xylose isomerase as a substrate. With the introduction of the xylulokinase gene, accordingly, metabolic activity of the xylose-metabolizing pathway in which the xylose isomerase is involved can be increased.

When *Saccharomyces cerevisiae* serves as a host of the recombinant yeast of the present invention, expression of the xylulokinase gene inherent in *Saccharomyces cerevisiae* may be enhanced, so that metabolic activity of the xylose-metabolizing pathway in which the xylose isomerase is involved can be increased. The nucleotide sequence of the xylulokinase gene inherentin *Saccharomyces cerevisiae* and the amino acid sequence of acetohydroxy acid reductoisomerase encoded by such gene are shown in SEQ ID NOs: 9 and 10, respectively.

The xylulokinase gene is not limited to the gene identified by SEQ ID NOs: 9 and 10. It maybe a paralogous gene or a homologous gene in the narrow sense having different nucleotide and amino acid sequences. The xylulokinase gene is not limited to the gene identified by SEQ ID NOs: 9 and 10. For example, it may be a gene comprising an amino acid sequence having 70% or higher, preferably 80% or higher, more preferably 90% or higher, and most preferably 95% or higher sequence similarity or identity with the amino acid sequence as shown in SEQ ID NO: 10 and encoding a protein having xylulokinase activity. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the xylulokinase gene is not limited to the gene identified by SEQ ID NOs: 9 and 10. For example, it may be a gene comprising an amino acid sequence derived from the amino acid sequence as shown in SEQ ID NO: 10 by substitution, deletion, insertion, or addition of one or several amino acids and encoding a protein having xylulokinase activity. The term "several" used herein refers to, for example, 2 to 30, preferably 2 to 20, more preferably 2 to 10, and most preferably 2 to 5.

Furthermore, the xylulokinase gene is not limited to the gene identified by SEQ ID NOs: 9 and 10. For example, it may be a gene hybridizing under stringent conditions to the full-length sequence or a partial sequence of a complementary strand of DNA comprising the nucleotide sequence as shown in SEQ ID NO: 9 and encoding a protein having xylulokinase activity. Under "stringent conditions," so-called specific hybrids are formed, but non-specific hybrids are not formed. Such conditions can be adequately determined with reference to, for example, Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42 degrees C. to 68 degrees C. and preferably 42 degrees C. to 65 degrees C., for example. Further specifically, the sodium concentration is 5×SSC (83 mM NaCl, 83 mM sodium citrate), and the temperature is 42 degrees C.

As described above, whether or not a gene comprising a nucleotide sequence that differs from the sequence shown in SEQ ID NO: 9 or a gene encoding an amino acid sequence that differs from the sequence shown in SEQ ID NO: 10 would function as the xylulokinase gene may be determined by, for example, preparing an expression vector comprising the gene of interest incorporated into an adequate site between a promoter and a terminator, transforming an *E. coli* host using such expression vector, and assaying xylulokinase activity of the protein expressed. The term "xylulokinase activity" refers to activity of converting xylulose into xylulose 5-phosphate. Thus, xylulokinase activity can be evaluated by preparing a solution containing xylulose and ATP as substrates, allowing the target protein to react at an adequate temperature, and measuring the amount of xylulose and ATP that had decreased and/or the amount of xylulose 5-phosphate that had been produced.

<Preparation of Recombinant Yeast>

The recombinant yeast of the present invention can be prepared by introducing the xylose isomerase gene into a host yeast and by modifying the host to produce a decreased amount of NADH as a result of the enzymatic reaction of acetohydroxy acid reductoisomerase. A host yeast is not particularly limited. A yeast that does not have xylose-metabolizing ability or a yeast that inherently has xylose-metabolizing ability may be used. Examples of host yeasts that can be used include, but are not particularly limited to, *Candida Shehatae*, *Pichia stipitis*, *Pachysolen tannophilus*, *Saccharomyces cerevisiae*, and *Schizosaccaromyces pombe*, with *Saccharomyces cerevisiae* being preferable. Examples of yeasts that inherently have xylose-metabolizing ability include, but are not particularly limited to, *Pichia stipitis*, *Candida tropicalis*, and *Candida prapsilosis*. Experimental yeast strains used from the viewpoint of experimental convenience or industrial(practical) strains used from the viewpoint of practical usefulness may also be used. Examples of industrial strains include yeast strains used for the production of wine, sake, and Shochu. Use of a host yeast strain having homothallic properties is preferable. According to the technique disclosed in JP 2009-34036 A, the multiple copies of a gene can be easily introduced into the genome with the use of a yeast having homothallic properties. The term "yeast having homothallic properties" is the same as the term "homothallic yeast." Yeasts having homothallic properties are not particularly limited, and any yeasts can be used. An example of a yeast having homothallic properties is, but is not limited to, the *Saccharomyces cerevisiae* OC-2 strain (NBRC2260). Examples of other yeasts having homothallic properties include an alcohol-producing yeast (Taiken No. 396, NBRC0216) (reference: "Alcohol kobo no shotokusei (Various properties of alcohol-producing yeast)," Shuken Kaiho, No. 37, pp. 18-22, 1998.8), an ethanol-producing yeast isolated in Brazil and in Japan (reference: "Brazil to Okinawa de bunri shita *Saccharomyces cerevisiae* yaseikabu no idengakuteki seishitsu (Genetic properties of wild-type *Saccharomyces cerevisiae* isolated in Brazil and in Okinawa)," the Journal of the Japan Society for Bioscience, Biotechnology, and Agrochemistry, Vol. 65, No. 4, pp. 759-762, 1991.4), and 180 (reference: "Alcohol Hakko-ryoku no tsuyoi kobo no screening (Screening of yeast having potent alcohol-fermenting ability)," the Journal of the Brewing Society of Japan, Vol. 82, No. 6, pp. 439-443, 1987.6). In addition, the HO gene may be introduced into a yeast exhibiting heterothallic phenotypes in an expressible manner, and the resulting strain can be used as a yeast having homothallic properties. That is, the term "yeast having homothallic properties" used herein also refers to a yeast into which the HO gene has been introduced in an expressible manner.

The *Saccharomyces cerevisiae* OC-2 strain is particularly preferable since it has heretofore been used for wine brewing, and the safety thereof has been verified. As described in the examples below, the *Saccharomyces cerevisiae* OC-2 strain is preferable in terms of its excellent promoter activity at high sugar concentration. In particular, the *Saccharomyces cerevisiae* OC-2 strain is preferable in terms of its excellent promoter activity for the pyruvate decarboxylase gene (PDC1) at high sugar concentrations.

Promoters of the xylose isomerase gene or mutant acetohydroxy acid reductoisomerase to be introduced are not particularly limited. For example, promoters of the glyceraldehyde-3-phosphate dehydrogenase gene (TDH3), the 3-phosphoglycerate kinase gene (PGK1), and the high-osmotic pressure response 7 gene (HOR7) can be used. The promoter of the pyruvate decarboxylasegene (PDC1) is particularly preferable in terms of its high capacity for expressing target genes in a downstream region at high levels.

Specifically, such gene may be introduced into the yeast genome together with an expression-regulating promoter or another expression-regulated region. Such gene may be introduced into a host yeast genome in such a manner that expression thereof is regulated by a promoter or another expression-regulated region of a gene that is inherently present therein.

The gene can be introduced into the genome by any conventional technique known as a yeast transformation technique. Specific examples include, but are not limited to, electroporation (Meth. Enzym., 194, p. 182, 1990), the spheroplast technique (Proc. Natl. Acad. Sci., U.S.A., 75, p. 1929, 1978), and the lithium acetate method (J. Bacteriology, 153, p. 163, 1983; Proc. Natl. Acad. Sci., U.S.A., 75, p. 1929, 1978; Methods in yeast genetics, 2000 Edition: A Cold Spring Harbor Laboratory Course Manual).

<Production of Ethanol>

When producing ethanol with the use of the recombinant yeast of the present invention, ethanol fermentation is carried out by culture in a medium containing at least xylose. Specifically, a medium in which ethanol fermentation is carried out contains at least xylose as a carbon source. Another carbon source, such as glucose, may be contained in a medium in advance.

Xylose contained in a medium used for ethanol fermentation can be derived from a biomass. In other words, a medium used for ethanol fermentation may be composed of a cellulosic biomass and a hemicellulase that generates xylose via saccharification of hemicellulose contained in the cellulosic biomass. The cellulosic biomass may have been subjected to a conventional pretreatment technique. Examples of pretreatment techniques include, but are not particularly limited to, degradation of a lignin with a microorganism and grinding of a cellulosic biomass. For example, a ground cellulosic biomass may be subjected to pretreatment, such as soaking thereof in a dilute sulfuric acid solution, alkaline solution, or ionic solution, hydrothermal treatment, or fine grinding. Thus, the efficiency of biomass saccharification can be improved.

When producing ethanol with the use of the recombinant yeast of the present invention, the medium may further comprise cellulose and cellulase. In such a case, the medium would contain glucose generated by the action of cellulase to cellulose. When a medium used for ethanol fermentation contains cellulose, such cellulose can be derived from a biomass. In other words, a medium used for ethanol fermentation may comprise cellulase that is capable of saccharifying cellulose contained in a cellulosic biomass.

A saccharified solution resulting from saccharification of a cellulosic biomass may be added to the medium used for ethanol fermentation. In such a case, the saccharified solution contains remaining cellulose, cellulase and xylose derived from hemicellulose contained in a cellulosic biomass.

As described above, the method for producing ethanol of the present invention comprises a step of ethanol fermentation involving the use of at least xylose as a saccharide source. According to the method for producing ethanol of the present invention, ethanol can be produced through ethanol fermentation using xylose as a saccharide source. According to the method for producing ethanol with the use of the recombinant yeast of the present invention, ethanol fermentation is followed by recovery of ethanol from the medium. Ethanol may be recovered by any conventional means without particular limitation. After the completion of the process of ethanol fermentation mentioned above, for example, a liquid layer containing ethanol is separated from a solid layer containing the recombinant yeast or solid matter via solid-solution separation. Thereafter, ethanol contained in a liquid layer is separated and purified by distillation, so that highly purified ethanol can be recovered. The degree of ethanol purification can be adequately determined in accordance with the purpose of use of the ethanol.

The method for producing ethanol of the present invention may employ the so-called simultaneous saccharification and fermentation process, in which the step of saccharification of cellulose contained in a medium with a cellulase proceeds simultaneously with the process of ethanol fermentation carried out with the use of saccharide sources (i.e., xylose and glucose generated by saccharification). In the simultaneous saccharification and fermentation process, the step of saccharification of a cellulosic biomass is carried out simultaneously with the step of ethanol fermentation.

Methods of saccharification are not particularly limited, and, for example, an enzymatic method involving the use of a cellulase preparation, such as cellulase or hemicellulase, may be employed. A cellulase preparation contains a plurality of enzymes involved in degradation of a cellulose chain and a hemicellulose chain, and it exhibits a plurality of types of activity, such as endoglucanase activity, endoxylanase activity, cellobiohydrolase activity, glucosidase activity, and xylosidase activity. A cellulase preparation is not particularly limited. For example, cellulase produced by *Trichoderma reesei* or *Acremonium cellulolyticus* can be used. A commercially available cellulase preparation may also be used.

In the simultaneous saccharification and fermentation process, a cellulase preparation and the above-described recombinant microorganism are added to a medium containing a cellulosic biomass (a biomass after pretreatment may be used), and the recombinant yeast is cultured at a given temperature. Culture may be carried out at any temperature without particular limitation, and the temperature may be 25 degrees C. to 45 degrees C., and preferably 30 degrees C. to 40 degrees C., from the viewpoint of efficiency for ethanol fermentation. The pH level of the culture solution is preferably 4 to 6. When conducting culture, stirring or shaking maybe carried out. Alternatively, the simultaneous saccharification and fermentation process may be carried out irregularly in such a manner that saccharification is first carried out a tan optimal temperature for an enzyme (40 degrees C. to 70 degrees C.), temperature is lowered to a given level (30 degrees C. to 40 degrees C.), and a yeast is then added thereto.

EXAMPLES

Hereafter, the present invention is described in greater detail with reference to the examples, although the technical scope of the present invention is not limited to these examples.

Example 1

In the present example, a recombinant yeast that had acquired xylose assimilation ability as a result of introduction of a xylose isomerase gene was modified, so that the resulting recombinant yeast would produce a decreased amount of NADH as a result of the enzymatic reaction of acetohydroxy acid reductoisomerase. The xylose assimilation ability and the ethanol productivity of such recombinant yeast were then evaluated. The recombinant yeast prepared in the present example has improved xylose-metabolizing activity as a result of introduction of the xylulokinase gene.

<Preparation of Vectors for Gene Introduction>

(1) Vector for XI and XKS1 Gene Introduction and GRE3 Gene Disruption

Figure 2:
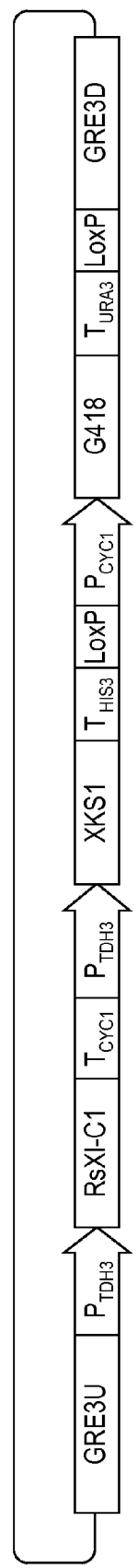
FIG. 2 is a structural diagram schematically showing pUC-GRE3U-P_TDH1-XI-T_CYC1-P_TDH3-XKS1-T_HIS3-LoxP-G418-LoxP-GRE3D.

As a vector capable of introducing the xylose isomerase gene derived from the intestinal protozoa of *Reticulitermes speratus* and the xylulokinase gene derived from the yeast into the GRE3 locus of a yeast while disrupting the GRE3 gene, pUC-GRE3U-P_TDH1-XI-T_CYC1-P_TDH3-XKS1-T_HIS3-LoxP-G418-LoxP-GRE3D was prepared (FIG. 2).

This vector was constructed so as to comprise: the xylose isomerase gene derived from the intestinal protozoa of *Reticulitermes speratus* in which the TDH1 promoter and the CYC1 terminator of the *Saccharomyces cerevisiae* BY4742 strain are added to the 5' side and the 3' side, respectively (RsXI-C1; see JP 2011-147445 A); the xylulokinase gene of the *Saccharomyces cerevisiae* BY4742 strain in which the TDH3 promoter and the HIS3 terminator of the *Saccharomyces cerevisiae* BY4742 strain are added to the 5' side and the 3' side, respectively (XKS1); regions to be integrated into the yeast genome via homologous recombination, i.e., a gene sequence of approximately 700 bp upstream from the 5' end of GRE3 (GRE3U) and a DNA sequence of approximately 800 bp downstream from the 3' end of GRE3 (GRE3D); and a marker gene sequence containing the G418 gene (the G418 marker). The marker gene is flanked by LoxP sequences, so that the marker can be removed from the marker gene sequence.

Each DNA sequence can be amplified with the use of the primers shown in Table 1. In order to allow DNA fragments to bind to each other, each target DNA fragment was amplified using the primers each prepared by adding a DNA sequence to a primer shown in Table 1 so as to overlap with an adjacent DNA sequence by about 15 bp, and a DNA fragment was allowed to bind to an adjacent DNA fragment using the In-Fusion HD Cloning Kit (Takara Bio). Thus, the vector was prepared.

(2) Vector for ilvC (NADP-Dependent) Gene Introduction

Figure 3:
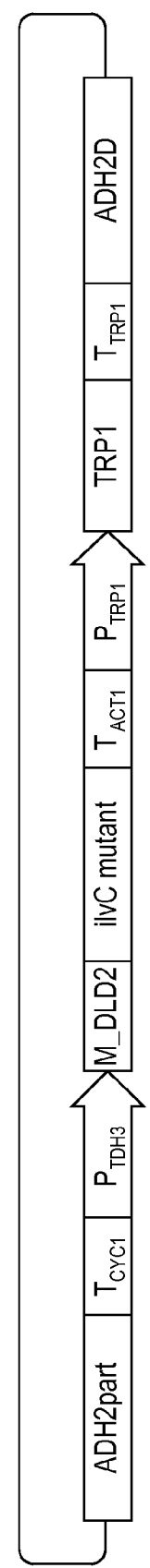
FIG. 3 is a structural diagram schematically showing pUC-ADH2part-T_CYC1-P_TDH3-M_DLD2-ilvC-mutant T_ACT1-TRP1-3U_ADH2.

As a vector for introducing the *E. coli*-derived NADP-dependent acetohydroxy acid reductoisomerase gene into a yeast, pUC-ADH2part-T_CYC1-P_TDH3-M_DLD2-ilvC-mutant T_ACT1-TRP1-3U_ADH2) was prepared (FIG. 3). This vector was constructed so as to comprise: a NADP-dependent mutant of the ilvC gene of acetohydroxy acid reductoisomerase derived from the *E. coli* K12 strain (the Genebank: 948286) in which the TDH3 promoter of the *Saccharomyces cerevisiae* BY4742 strain and a fragment of the DLD2 gene that is predicted to be a mitochondrial-targeting signal peptide (i.e., 135 nucleotides from the 5' end, M_DLD2) are added to the 5' side and the ACT1 terminator is added to the 3' side; regions to be integrated into the yeast genome via homologous recombination, i.e., a gene sequence of approximately 450 bp upstream from the 3'end (ADH2part) and a DNA sequence of approximately 700 bp downstream from the 3' end (ADH2D) of the ADH2 gene; the CYC1 terminator region as the ADH2 terminator; and a marker gene sequence containing the TRP1 gene (the TRP1 marker). In the present example, a gene encoding an amino acid sequence having the mutations R68D, K69L, K75V, and R76D (Arch. Biochem. Biophys., 338, 83-89, 1997), and comprising a nucleotide sequence in which codons had been altered in accordance with the codon usage frequency of the yeast was used. In the present example, the NADP-dependent ilvC gene was fully synthesized. In the present example, another NADP-dependent ilvC gene encoding an amino acid sequence having the mutations A71S, R76D, S78D, Q110V, D146G, and G185R (U.S. Pat. No. 8,097,440), and comprising a nucleotide sequence in which codons had been altered in accordance with the codon usage frequency of the yeast was used. In the present example, also, this NADP-dependent ilvC gene was fully synthesized.

Each DNA sequence can be amplified with the use of the primers shown in Table 1. In order to allow DNA fragments to bind to each other, each target DNA fragment was amplified using the primers each prepared by adding a DNA sequence to a primer shown in Table 1 so as to overlap with an adjacent DNA sequence by about 15 bp, and a DNA fragment was allowed to bind to an adjacent DNA fragment using the In-Fusion HD Cloning Kit (Takara Bio). Thus, the vector was prepared.

(3) Vector for ILV5 Gene Disruption

Figure 4:
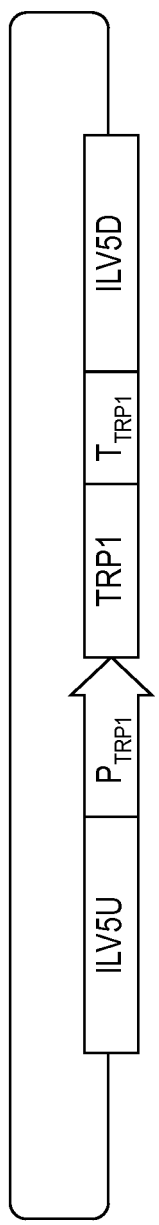
FIG. 4 is a structural diagram schematically showing pUC-ILV5U-TRP1-ILV5D.

A vector for disrupting the ILV5 gene, pUC-ILV5U-TRP1-ILV5D, was prepared (FIG. 4). This vector was constructed so as to comprise: a region to be integrated into the yeast genome via homologous recombination and a region for disruption of acetohydroxy acid reductoisomerase (ILV5) gene, i.e., a DNA sequence of approximately 850 bp upstream of the ILV5 gene (ILV5U) and a DNA sequence of approximately 800 bp downstream of the ILV5 gene (ILV5D); and a marker gene sequence containing TRP1 (the TRP1 marker).

Each DNA sequence can be amplified with the use of the primers shown in Table 1. In order to allow DNA fragments to bind to each other, each target DNA fragment was amplified using the primers each prepared by adding a DNA sequence to a primer shown in Table 1 so as to overlap with an adjacent DNA sequence by about 15 bp, and a DNA fragment was allowed to bind to an adjacent DNA fragment using the In-Fusion HD Cloning Kit (Takara Bio). Thus, the vector was prepared.

(4) Control Vector (Marker Gene Only)

Figure 5:
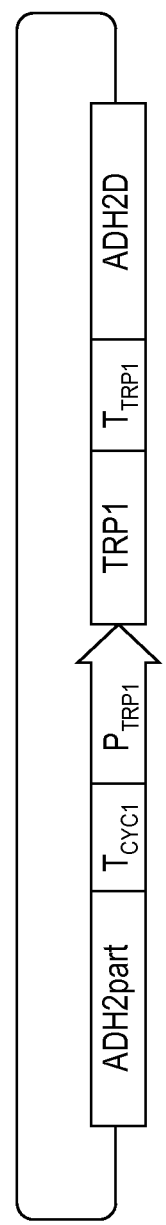
FIG. 5 is a structural diagram schematically showing pUC-ADH2part-T_CYC1-TRP1-ADH2D.

A control vector for introducing a marker gene only, pUC-ADH2part-T_CYC1-TRP1-ADH2D, was prepared (FIG. 5). This vector was constructed so as to comprise: regions to be integrated into the yeast genome via homologous recombination, i.e., a gene sequence of approximately 450 bp upstream from the 3' end (ADH2part) and a DNA sequence of approximately 700 bp downstream from the 3' end (ADH2D) of the ADH2 gene; the CYC1 terminator sequence as the ADH2 terminator; and a marker gene sequence containing TRP1 (the TRP1 marker).

Each DNA sequence can be amplified with the use of the primers shown in Table 1. In order to allow DNA fragments to bind to each other, each target DNA fragment was amplified using the primers each prepared by adding a DNA sequence to a primer shown in Table 1 so as to overlap with an adjacent DNA sequence by about 15 bp, and a DNA fragment was allowed to bind to an adjacent DNA fragment using the In-Fusion HD Cloning Kit (Takara Bio). Thus, the vector was prepared.

TABLE 1

| Amplified DNA fragment | Primer sequence | SEQ ID NO |
|---|---|---|
| pUC-GRE3U-P_TDH1-XI-T_CYC1-P_TDH3-XKS1-T_HIS3-LoxP-G418-LoxP-GRE3D | | |
| TDH1 promoter | 5'-GGAAATTTTTTAAAGCTTCCCTTTTACAGTGCTTC-3' | 11 |
| | 5'-AAAAATTTGAGACATTTTGTTTTGTGTGTAAATTTAGTGAAG-3' | 12 |
| RsXI-C1 | 5'-ATGTCTCAAATTTTTAAGGATATCCCAG-3' | 13 |
| | 5'-GGGGCCTGTCTTAAGTTATTGAAACAAAATTTGGTTAATAATACTTTC-3' | 14 |
| CYC1 terminator | 5'-CTTAAGACAGGCCCCTTTTCCTTTG-3' | 15 |
| | 5'-TAACATTCAACGCTACTGCAGGAATTCGATATC-3' | 16 |
| TDH3 promoter | 5'-TAGCGTTGAATGTTAGCGTCAACAAC-3' | 17 |
| | 5'-TACTGAACACAACATTTTGTTTGTTTATGTGTGTTTATTCG-3' | 18 |
| XKS1 | 5'-ATGTTGTGTTCAGTAATTCAGAGACAG-3' | 19 |
| | 5'-AAATAATCGGTGTCATTAGATGAGAGTCTTTTCCAGTTC-3' | 20 |
| HIS3 terminator | 5'-TGACACCGATTATTTAAAGCTGCAG-3' | 21 |
| | 5'-AGAGCGCGCCTCGTTC-3' | 22 |
| GRE3U | 5'-TGGGAATATTACCGCTCGAAG-3' | 23 |
| | 5'-CTTTAAAAAATTTCCAATTTTCCTTTACG-3' | 24 |
| GRE3D | 5'-AACGAGGCGCGCTCTTCCAGCCAGTAAAATCCATAC-3' | 25 |
| | 5'-AAGGGGGAAGGTGTGGAATC-3' | 26 |
| pUC-ADH2part-T_CYC1-P_TDH3-M_DLD2-ilvC-mutant-T_ACT1-TRP1-3U_ADH2 | | |
| TDH3 promoter | 5'-TAGCGTTGAATGTTAGCGTCAACAAC-3' | 27 |
| | 5'-TTTGTTTGTTTATGTGTGTTTATTCGAAACTAAGTTCTTGG-3' | 28 |
| M_DLD2 | 5'-ATGCTAAGAAACATTTGGTGAGAAG-3' | 29 |
| | 5'-AGTCAGTCTGGTTTGTATCTTG-3' | 30 |
| ilvC mutant | 5'-ATGGCAAACTACTTCAACACTTTGAATTTG-3' | 31 |
| | 5'-TTAACCTGCAACAGCGATTC-3 | 32 |
| ADH2part | 5'-CCAACTGTCCTCACGCTGAC-3' | 33 |
| | 5'-CTTATTTAGAAGTGTCAACAACGTATCTACC-3' | 34 |
| ADH2D | 5'-GCGGATCTCTTATGTCTTTACGATTTATAGTTTTC-3' | 35 |
| | 5'-GAGGGTTGGGCATTCATCAG-3' | 36 |
| pUC-ILV5U-TRP1-ILV5D | | |
| CYC1 terminator | 5'-CTTAAGACAGGCCCCTTTTCCTTTG-3' | 37 |
| | 5'-CTGCAGGAATTCGATATCAAGCTTATC-3' | 38 |
| TRP1 marker | 5'-ACGACATTACTATATATATAATATAGGAAGCATTTAATAG-3' | 39 |
| | 5'-GACATAAGAGATCCGCAGG-3' | 40 |
| ILV5U | 5'-AAACGGCCAGTAGCCAAGAC-3' | 41 |
| | 5'-ACTCCAAGCTGCCTTTGTGTGC-3' | 42 |
| ILV5D | 5'-AGAGGAAAATAATATCAAGTGCTGGAAAC-3' | 43 |
| | 5'-CCGGAGGCTTTCAATTGTTC-3' | 44 |
| pUC-ADH2part-T_CYC1-TRP1-ADH2D | | |
| CYC1 terminator | 5'-CTTAAGACAGGCCCCTTTTCCTTTG-3' | 45 |
| | 5'-ATATAGTAATGTCGTCTGCAGGAATTCGATATCAAG-3' | 46 |
| TRP1 marker | 5'-ACGACATTACTATATATATAATATAGGAAGCATTTAATAG-3' | 47 |
| | 5'-ACATAAGAGATCCGCAGGCAAGTGCACAAACAATAC-3' | 48 |
| ADH2part | 5'-CCAACTGTCCTCACGCTGAC-3' | 49 |
| | 5'-GGGGCCTGTCTTAAGCTTATTTAGAAGTGICAACAACG-3' | 50 |
| ADH2D | 5'-GCGGATCTCTTATGTCTTTACGATTTATAGTTTTC-3' | 51 |
| | 5'-GAGGGTTGGGCATTCATCAG-3' | 52 |

<Preparation of Yeasts Comprising Vectors Introduced Thereinto>

The diploid yeasts auxotrophic for tryptophan, *Saccharomyces cerevisiae* OC2-T strain (Saitoh, S. et al., J. Ferment. Bioeng., 1996, vol. 81, pp. 98-103), were designated as host strains. Yeasts were transformed using the Frozen-EZ Yeast Transformation II (ZYMO RESEARCH) in accordance with the protocols included therein.

At the outset, a region to be subjected to homologous recombination of the vector, pUC-5U_GRE3-P_TDH1-XI-T_CYC1-P_TDH3-XKS1-T_HIS3-LoxP-G418-LoxP-3U_GRE3, was amplified by PCR, the resulting fragment was transformed into the OC2-T strains, the resultants were applied to a tryptophan-free SD agar medium, and the grown colonies were then subjected to purification. The purified strain was designated as the Uz979 strain. The resulting strain was allowed to sporulate in a sporulation medium (1% potassium phosphate, 0.1% yeast extract, 0.05% glucose, and 2% agar), so as to cause diploidization with the utilization of homothallic properties. Diploid strain containing the XI and XKS1 genes integrated into and the GRE3 gene disrupted in the GRE3 genetic loci of the chromosomes was obtained and designated as the Uz979 strain.

Subsequently, regions subjected to homologous recombination of the vector, pUC-ADH2part-T_CYC1-P_TDH3-M_DLD2-ilvC-mutant R68D K69L K75V R76D-T_ACT1-TRP1-3U_ADH2, pUC-ADH2part-T_CYC1-P_TDH3-M_DLD2-ilvC-mutant A71S R76D S78D Q110V D146G G185R-T_ACT1-TRP1-3U_ADH2, pUC-ILV5U-TRP1-ILV5D, or pUC-ADH2part-T_CYC1-TRP1-ADH2D, were amplified by PCR, the resulting fragments were transformed into the Uz979 strain, the resultants were applied to a tryptophan-free SD agar medium, and the grown colonies were subjected to purification. The purified strains were designated as the Uz999, Uz1000, Uz1089, and Uz1034 strains, respectively. Heterozygous recombination (in one copy) was observed in each strain.

<Fermentation Test>

Two strains exhibiting high fermentation ability were selected from each of the Uz999, Uz1000, Uz1089, and Uz1034 strains obtained in the manner described above, and the selected strains were subjected to a fermentation test in flasks in the manner described below. At the outset, the test strains were introduced into 100-ml baffled flasks each containing 20 ml of YPD liquid medium containing glucose at 20 g/l (10 g/l yeast extract, 20 g/l peptone, and 20 g/l glucose), and culture was conducted at 30 degrees C. and 120 rpm for 24 hours. The strains were collected and introduced into 20-ml flasks each containing 10 ml of the D5X65YPAc3 medium (5 g/l glucose, 65 g/l xylose, 10 g/l yeast extract, 20 g/l peptone, and 3 g/l acetic acid) (cell density: 0.3 g of dry cells/). The fermentation test was carried out via shake culture (80 rpm; shake width: 35 mm; 30 degrees C.). Each flask was stoppered with a rubber cap comprising a needle (inner diameter: 1.5 mm), and anaerobic conditions inside the flask were maintained by mounting a check valve at the tip of the needle.

Sampling was carried out 90 hours, 114 hours, and 138 hours after the initiation of fermentation, and the xylose concentration and the ethanol concentration in the fermentation liquid were assayed via HPLC (LC-10A, Shimadzu Seisakusho) under the conditions described below. From among the data obtained through three sampling instances, the data attained when the highest ethanol concentration was observed were employed as the results of the fermentation test (and such data represent the average of two strains).

[HPLC Conditions]
Column: AminexHPX-87H
Mobile phase: 0.01N $H_2SO_4$
Flow rate: 0.6 ml/min
Temperature: 30 degrees C.
Detector: differential refractometer (RID-10A)

<Results of Fermentation Test>

The results of the fermentation test are shown in Table 2.

TABLE 2

| | Control Uz1034 | ilvC mutant Uz999 R68D K69L K75V R76D | ilvC mutant Uz1000 A71S R76D S78D Q110V D146G G185R | ILV5 hetero-disrupted Uz1089 |
|---|---|---|---|---|
| Ethanol concentration (g/l) | 2.07 | 7.16 | 6.92 | 6.48 |
| Xylose concentration (g/l) | 57.2 | 35.3 | 37 | 40.1 |

As is apparent from Table 2, the Uz999 strain and the Uz1000 strain into which the NADP-dependent ilvC genes had been introduced and the Uz1089 strain comprising a hetero-disruption of the endogenous ILV5 gene showed remarkable improvement in the rate of xylose assimilation, compared with the control Uz1034 strain, and ethanol productivity was improved as a consequence. On the basis of the results demonstrated above, xylose assimilation ability and ethanol productivity were found to be remarkably improved in a recombinant yeast having xylose assimilation ability into which the xylose isomerase gene had been introduced by reducing the amount of NADH produced as a result of the enzymatic reaction of acetohydroxy acid reductoisomerase.

SEQUENCE LISTING

PH-5740PCT sequence listing.txt

The invention claimed is:

1. A recombinant yeast into which a xylose isomerase gene has been introduced, and wherein in said yeast, an endogenous gene encoding acetohydroxy acid reductoisomerase is heterozygously disrupted, or a gene encoding a mutant acetohydroxy acid reductoisomerase with lowered NAD+ dependence and enhanced NADP+ dependence is introduced, and wherein said yeast does not contain a xylose reductase gene or a xylitol dehydrogenase gene.

2. The recombinant yeast according to claim 1, wherein the endogenous gene encoding acetohydroxy acid reductoisomerase encodes protein (a) or (b) below:
   (a) a protein comprising the amino acid sequence as shown in SEQ ID NO: 2; or
   (b) a protein comprising an amino acid sequence having 80% or higher identity with the amino acid sequence as shown in SEQ ID NO: 2 and having enzymatic activity of converting 2-acetolactate and $NAD^+$ into 2,3-dihydroxy-isovalerate and NADH, respectively.

3. The recombinant yeast according to claim 1, wherein the gene encoding the mutant acetohydroxy acid reductoisomerase encodes protein (a) or (b) below:
   (a) protein comprising the amino acid sequence as shown in SEQ ID NO: 4 or 6; or
   (b) protein comprising an amino acid sequence having 80% or higher identity with the amino acid sequence as shown in SEQ ID NO: 4 or 6 and having enzymatic activity of converting 2-acetolactate and $NADP^{30}$ into 2,3-dihydroxy-isovalerate and NADPH, respectively.

4. The recombinant yeast according to claim 1, wherein the xylose isomerase gene encodes protein (a) or (b) below:
   (a) a protein comprising the amino acid sequence as shown in SEQ ID NO: 8; or
   (b) a protein comprising an amino acid sequence having 80% or higher identity with the amino acid sequence as shown in SEQ ID NO: 8 and having enzymatic activity of converting xylose into xylulose.

5. A method for producing ethanol comprising a step of culturing the recombinant yeast according to claim 1 in a xylose-containing medium to perform ethanol fermentation.

* * * * *